US012765975B2

(12) United States Patent
Moalem et al.

(10) Patent No.: US 12,765,975 B2
(45) Date of Patent: Oct. 20, 2026

(54) ACCURATE SCANNING OF PATIENT BITE

(71) Applicant: Align Technology, Inc., San Jose, CA (US)

(72) Inventors: Yosi Moalem, Nes-Ziona (IL); Ofer Saphier, Rechovot (IL); Moti Ben-Dov, Tel Mond (IL)

(73) Assignee: Align Technology, Inc., San Jose, CA (US)

( * ) Notice: Subject to any disclaimer, the term of this patent is extended or adjusted under 35 U.S.C. 154(b) by 202 days.

(21) Appl. No.: 18/409,860

(22) Filed: Jan. 11, 2024

(65) Prior Publication Data

US 2024/0245495 A1 Jul. 25, 2024

Related U.S. Application Data

(60) Provisional application No. 63/481,366, filed on Jan. 24, 2023.

(51) Int. Cl.

*A61C 9/00* (2006.01)
*A61B 1/00* (2006.01)
*A61B 1/24* (2006.01)
*A61C 19/05* (2006.01)

(52) U.S. Cl.

CPC ............ *A61C 9/0053* (2013.01); *A61C 19/05* (2013.01); *A61B 1/00011* (2013.01); *A61B 1/00135* (2013.01); *A61B 1/24* (2013.01)

(58) Field of Classification Search

CPC ....... A61C 9/0053; A61C 19/05; A61C 7/002; A61B 1/00011; A61B 1/00135; A61B 1/24; A61B 5/0088; A61B 1/00172; A61B 1/00194; A61B 1/247; A61B 5/1079; A61B 5/4547

See application file for complete search history.

(56) References Cited

U.S. PATENT DOCUMENTS

| | | | |
|---|---|---|---|
| 6,099,314 | A | 8/2000 | Kopelman et al. |
| 6,334,772 | B1 | 1/2002 | Taub et al. |
| 6,334,853 | B1 | 1/2002 | Kopelman et al. |
| 6,463,344 | B1 | 10/2002 | Pavlovskaia et al. |
| 6,542,249 | B1 | 4/2003 | Kofman et al. |
| 6,633,789 | B1 | 10/2003 | Nikolskiy et al. |
| 6,664,986 | B1 | 12/2003 | Kopelman et al. |
| 6,697,164 | B1 | 2/2004 | Babayoff et al. |
| 6,845,175 | B2 | 1/2005 | Kopelman et al. |

(Continued)

*Primary Examiner* — Stephen R Koziol
*Assistant Examiner* — Michael Kim Maiden
(74) *Attorney, Agent, or Firm* — Lowenstein Sandler LLP

(57) ABSTRACT

An intraoral scanning system comprises an intraoral scanner and a computing device. The intraoral scanner is to configured to generate intraoral scan data of a bite of a patient. The computing device is configured to receive the intraoral scan data of the bite of the patient during scanning of the bite of the patient, wherein each datum of the intraoral scan data shows a portion of a lower dental arch and a portion of an upper dental arch of the patient. The computing device determines a difference in a relative position of the lower dental arch to the upper dental arch between at least a first datum of the intraoral scan data and a second datum of the intraoral scan data and performs a remedial action responsive to determining that the difference in the relative position of the lower dental arch to the upper dental arch exceeds a difference threshold.

26 Claims, 15 Drawing Sheets

(56) References Cited

U.S. PATENT DOCUMENTS

| | | | |
|---|---|---|---|
| 6,979,196 B2 | 12/2005 | Nikolskiy et al. | |
| 7,030,383 B2 | 4/2006 | Babayoff et al. | |
| 7,202,466 B2 | 4/2007 | Babayoff et al. | |
| 7,255,558 B2 | 8/2007 | Babayoff et al. | |
| 7,286,954 B2 | 10/2007 | Kopelman et al. | |
| 7,319,529 B2 | 1/2008 | Babayoff | |
| 7,373,286 B2 | 5/2008 | Nikolskiy et al. | |
| 7,507,088 B2 | 3/2009 | Taub et al. | |
| 7,545,372 B2 | 6/2009 | Kopelman et al. | |
| 7,698,068 B2 | 4/2010 | Babayoff | |
| 7,916,911 B2 | 3/2011 | Kaza et al. | |
| 8,108,189 B2 | 1/2012 | Chelnokov et al. | |
| 8,244,028 B2 | 8/2012 | Kuo et al. | |
| 8,587,582 B2 | 11/2013 | Matov et al. | |
| 8,948,482 B2 | 2/2015 | Levin | |
| D742,518 S | 11/2015 | Barak et al. | |
| 9,192,305 B2 | 11/2015 | Levin | |
| 9,261,356 B2 | 2/2016 | Lampert et al. | |
| 9,261,358 B2 | 2/2016 | Atiya et al. | |
| 9,299,192 B2 | 3/2016 | Kopelman | |
| D760,901 S | 7/2016 | Barak et al. | |
| 9,393,087 B2 | 7/2016 | Moalem | |
| 9,408,679 B2 | 8/2016 | Kopelman | |
| 9,431,887 B2 | 8/2016 | Boltanski | |
| 9,439,568 B2 | 9/2016 | Atiya et al. | |
| 9,451,873 B1 | 9/2016 | Kopelman et al. | |
| D768,861 S | 10/2016 | Barak et al. | |
| D771,817 S | 11/2016 | Barak et al. | |
| 9,491,863 B2 | 11/2016 | Boltanski | |
| D774,193 S | 12/2016 | Makmel et al. | |
| 9,510,757 B2 | 12/2016 | Kopelman et al. | |
| 9,660,418 B2 | 5/2017 | Atiya et al. | |
| 9,668,829 B2 | 6/2017 | Kopelman | |
| 9,675,430 B2 | 6/2017 | Verker et al. | |
| 9,693,839 B2 | 7/2017 | Atiya et al. | |
| 9,717,402 B2 | 8/2017 | Lampert et al. | |
| 9,724,177 B2 | 8/2017 | Levin | |
| 9,844,426 B2 | 12/2017 | Atiya et al. | |
| 10,076,389 B2 | 9/2018 | Wu et al. | |
| 10,098,714 B2 | 10/2018 | Kuo | |
| 10,108,269 B2 | 10/2018 | Sabina et al. | |
| 10,111,581 B2 | 10/2018 | Makmel | |
| 10,111,714 B2 | 10/2018 | Kopelman et al. | |
| 10,123,706 B2 | 11/2018 | Elbaz et al. | |
| 10,136,972 B2 | 11/2018 | Sabina et al. | |
| 10,380,212 B2 | 8/2019 | Elbaz et al. | |
| 10,390,913 B2 | 8/2019 | Sabina et al. | |
| 10,453,269 B2 | 10/2019 | Furst | |
| 10,456,043 B2 | 10/2019 | Atiya et al. | |
| 10,499,793 B2 | 12/2019 | Ozerov et al. | |
| 10,504,386 B2 | 12/2019 | Levin et al. | |
| 10,507,087 B2 | 12/2019 | Elbaz et al. | |
| 10,517,482 B2 | 12/2019 | Sato et al. | |
| 10,695,150 B2 | 6/2020 | Kopelman et al. | |
| 10,708,574 B2 | 7/2020 | Furst et al. | |
| 10,772,506 B2 | 9/2020 | Atiya et al. | |
| 10,813,727 B2 | 10/2020 | Sabina et al. | |
| 10,888,399 B2 | 1/2021 | Kopelman et al. | |
| 10,952,816 B2 | 3/2021 | Kopelman | |
| 10,980,613 B2 | 4/2021 | Shanjani et al. | |
| 11,013,581 B2 | 5/2021 | Sabina et al. | |
| D925,739 S | 7/2021 | Shalev et al. | |
| 11,096,765 B2 | 8/2021 | Atiya et al. | |
| 11,238,586 B2 | 2/2022 | Minchenkov et al. | |
| 11,367,192 B2 | 6/2022 | Kopelman et al. | |
| 11,455,727 B2 | 9/2022 | Minchenkov et al. | |
| 11,478,132 B2 | 10/2022 | Kopelman et al. | |
| 11,563,929 B2 | 1/2023 | Saphier et al. | |
| 11,633,268 B2 | 4/2023 | Moalem et al. | |
| 11,707,238 B2 | 7/2023 | Moshe et al. | |
| RE49,605 E | 8/2023 | Kopelman | |
| 11,744,681 B2 | 9/2023 | Kopelman et al. | |
| 11,759,277 B2 | 9/2023 | Shalev et al. | |
| 11,896,461 B2 | 2/2024 | Saphier et al. | |
| 11,937,996 B2 | 3/2024 | Peleg | |
| 2008/0057466 A1* | 3/2008 | Jordan | A61C 9/0046 433/69 |
| 2016/0008116 A1* | 1/2016 | Glinec | G06T 19/20 433/29 |
| 2018/0168781 A1* | 6/2018 | Kopelman | A61C 9/0053 |
| 2021/0059796 A1 | 3/2021 | Weiss et al. | |
| 2021/0121049 A1 | 4/2021 | Rudnitsky et al. | |
| 2021/0137653 A1 | 5/2021 | Saphier et al. | |
| 2021/0196152 A1 | 7/2021 | Saphier et al. | |
| 2021/0321872 A1 | 10/2021 | Saphier et al. | |
| 2023/0048005 A1* | 2/2023 | Wu | A61C 19/05 |
| 2024/0268929 A1* | 8/2024 | Lee | A61C 9/00 |

* cited by examiner

1050

ACCURATE SCANNING OF PATIENT BITE

RELATED APPLICATIONS

This patent application claims the benefit under 35 U.S.C. § 119(e) of U.S. Provisional Application No. 63/481,366, filed Jan. 24, 2023, which is incorporated by reference herein.

TECHNICAL FIELD

Embodiments of the present disclosure relate to the field of dentistry and, in particular, to methods and systems for accurate scanning of a patient bite using an intraoral scanner.

BACKGROUND

For both restorative and orthodontic dentistry it can be beneficial to generate accurate three-dimensional (3D) models of a patient's upper and lower dental arches and to determine relative positions of the patient's upper and lower dental arches. Such 3D models are generated based on intraoral scanning performed using an intraoral scanner. However, even with the most advanced and accurate intraoral scanners, the 3D models often suffer from inaccuracies. A major contributor to inaccuracies of the 3D models is scanning of a patient bite.

SUMMARY

In a first implementation, a method of scanning an oral cavity of a patient, comprises: scanning an upper dental arch of the patient using an intraoral scanner; scanning a lower dental arch of the patient using the intraoral scanner; and scanning a bite of the patient using the intraoral scanner, the scanning of the bite comprising: directing the patient to close their jaw prior to insertion of the intraoral scanner into the oral cavity; retracting a left cheek of the patient and inserting the intraoral scanner between the left cheek and the closed jaw; scanning a left side of the upper dental arch and the lower dental arch while the patient's jaw remains closed; removing the intraoral scanner from the left cheek while the patient's jaw remains closed; retracting a right cheek of the patient and inserting the intraoral scanner between the right cheek and the closed jaw; and scanning a right side of the upper dental arch and the lower dental arch while the patient's jaw remains closed.

A second implementation may further extend the first implementation. In the second implementation, the method further comprises: generating a first 3D model of the upper dental arch based on intraoral scans captured during scanning of the upper dental arch; generating a second 3D model of the lower dental arch based on intraoral scans captured during scanning of the lower dental arch; and determining a relative position and orientation of the first 3D model of the upper dental arch to the second 3D model of the lower dental arch based on intraoral scans captured during scanning of the bite of the patient.

A third implementation may further extend the first or second implementation. In the third implementation, the left cheek and the right cheek are retracted using a cheek retraction tool.

A fourth implementation may further extend the first or second implementation. In the fourth implementation, the left cheek and the right cheek are retracted using the intraoral scanner.

A fifth implementation may further extend any of the first through fourth implementations. In the fifth implementation, the method further comprises: determining whether the lower dental arch moved relative to the upper dental arch by more than a threshold amount during scanning of the bite of the patient; and performing one or more remedial actions responsive to determining that the lower dental arch moved relative to the upper dental arch by more than the threshold amount.

In a sixth implementation, a method of scanning an oral cavity of a patient comprises: scanning an upper dental arch of the patient using an intraoral scanner; scanning a lower dental arch of the patient using the intraoral scanner; and scanning a bite of the patient using the intraoral scanner, the scanning of the bite comprising: retracting a left cheek of the patient and inserting a first sleeve for the intraoral scanner between the left cheek and a jaw of the patient; retracting a right cheek of the patient and inserting a second sleeve for the intraoral scanner between the right cheek and the jaw of the patient; and performing the following while the jaw remains closed: inserting the intraoral scanner into the first sleeve; scanning a left side of the upper dental arch and the lower dental arch; removing the intraoral scanner from the first sleeve and from the left cheek; inserting the intraoral scanner into the second sleeve; and scanning a right side of the upper dental arch and the lower dental arch.

A seventh implementation may further extend the sixth implementation. In the seventh implementation, the method further comprises: generating a first 3D model of the upper dental arch based on intraoral scans captured during scanning of the upper dental arch; generating a second 3D model of the lower dental arch based on intraoral scans captured during scanning of the lower dental arch; and determining a relative position and orientation of the first 3D model of the upper dental arch to the second 3D model of the lower dental arch based on intraoral scans captured during scanning of the bite of the patient.

An eighth implementation may further extend the sixth or seventh implementation. In the eighth implementation, the method further comprises: determining whether the lower dental arch moved relative to the upper dental arch by more than a threshold amount during scanning of the bite of the patient; and performing one or more remedial actions responsive to determining that the lower dental arch moved relative to the upper dental arch by more than the threshold amount.

In a ninth implementation, a method comprises: receiving intraoral scan data generated by an intraoral scanner during scanning of a bite of a patient, wherein each datum of the intraoral scan data shows a portion of a lower dental arch and a portion of an upper dental arch of the patient; determining a difference in a relative position of the lower dental arch to the upper dental arch between at least a first datum of the intraoral scan data and a second datum of the intraoral scan data; and performing a remedial action responsive to determining that the difference in the relative position of the lower dental arch to the upper dental arch exceeds a difference threshold. The ninth implementation may stand alone, or may be performed commensurate with any of the first through eighth implementations.

A $10^{th}$ implementation may further extend the ninth implementation. In the $10^{th}$ implementation the method further comprises: determining, for at least the first datum and the second datum of the intraoral scan data, the relative position of the lower dental arch to the upper dental arch.

An $11^{th}$ implementation may further extend the ninth or $10^{th}$ implementation. In the $11^{th}$ implementation, the intraoral scan data comprises at least one of a plurality of intraoral scans or a plurality of two-dimensional (2D) images, the method further comprising: receiving a first additional plurality of intraoral scans generated by the intraoral scanner during scanning of the upper dental arch of the patient; generating a first three-dimensional (3D) model of the upper dental arch of the patient using the first additional plurality of intraoral scans; receiving a second additional plurality of intraoral scans generated by the intraoral scanner during scanning of the lower dental arch of the patient; and generating a second 3D model of the lower dental arch of the patient using the second plurality of intraoral scans.

A 12$^{th}$ implementation may further extend the ninth through 11$^{th}$ implementations. In the 12$^{th}$ implementation, the first datum comprises a first 2D image of the plurality of 2D images and the second datum comprises a second 2D image of the plurality of 2D images.

A 13$^{th}$ implementation may further extend the 11$^{th}$ or 12$^{th}$ implementations. In the 13$^{th}$ implementation, determining the relative position of the lower dental arch to the upper dental arch for the first 2D image comprises: registering a first region of the first 2D image showing a portion of the upper dental arch to the first 3D model of the upper dental arch; and registering a second region of the first 2D image showing a portion of the lower dental arch to the second 3D model of the lower dental arch.

A 14$^{th}$ implementation may further extend any of the 11$^{th}$ through 13$^{th}$ implementations. In the 14$^{th}$ implementation, the first datum comprises a first intraoral scan of the plurality of intraoral scans and the second datum comprises a second intraoral scan of the plurality of intraoral scans.

A 15$^{th}$ implementation may further extend the 14$^{th}$ implementation. In the 15$^{th}$ implementation, determining the relative position of the lower dental arch to the upper dental arch for the first intraoral scan comprises: registering a first region of the first intraoral scan showing a portion of the upper dental arch to the first 3D model of the upper dental arch; and registering a second region of the first intraoral scan showing a portion of the lower dental arch to the second 3D model of the lower dental arch.

A 16$^{th}$ implementation may further extend any of the 9$^{th}$ through 15$^{th}$ implementations. In the 16$^{th}$ implementation, the intraoral scan data comprises a plurality of intraoral scans, wherein the first datum comprises a first intraoral scan of the plurality of intraoral scans, wherein the second datum comprises a second intraoral scan of the plurality of intraoral scans, and wherein determining the difference in the relative position of the lower dental arch to the upper dental arch between at least the first datum of the intraoral scan data and the second datum of the intraoral scan data comprises: identifying a first region of the first intraoral scan that shows a first portion of the upper dental arch; identifying a second region of the first intraoral scan that shows a first portion of the lower dental arch; determining a first relative position of the upper dental arch and the lower dental arch in the first intraoral scan based on the first region and the second region; identifying a third region of the second intraoral scan that shows a second portion of the upper dental arch; identifying a fourth region of the second intraoral scan that shows a second portion of the lower dental arch; determining a second relative position of the upper dental arch and the lower dental arch in the second intraoral scan based on the third region and the fourth region; and comparing the second relative position of the upper dental arch and the lower dental arch to the first relative position of the upper dental arch and the lower dental arch.

A 17$^{th}$ implementation may further extend any of the 9$^{th}$ through 16$^{th}$ implementations. In the 17$^{th}$ implementation, performing the remedial action comprises notifying a user that the lower dental arch has moved relative to the upper dental arch during scanning of the bite of the patient.

An 18$^{th}$ implementation may further extend any of the 9$^{th}$ through 17$^{th}$ implementations. In the 18$^{th}$ implementation, the method further comprises: averaging the relative position of the lower dental arch to the upper dental arch from the first datum and the relative position of the lower dental arch to the upper dental arch from the second datum responsive to determining that the difference is below the difference threshold.

A 19$^{th}$ implementation may further extend any of the 9$^{th}$ through 17$^{th}$ implementations. In the 19$^{th}$ implementation, performing the remedial action comprises recommending rescanning of the bite of the patient.

A 20$^{th}$ implementation may further extend any of the 9$^{th}$ through 19$^{th}$ implementations. In the 20$^{th}$ implementation, the method further comprises: determining a first subset of the intraoral scan data having a first relative position of the lower dental arch to the upper dental arch and a second subset of the intraoral scan data having a second relative position of the lower dental arch to the upper dental arch.

A 21$^{st}$ implementation may further extend the 20$^{th}$ implementation. In the 21$^{st}$ implementation, the method further comprises: prompting a user to select the first relative position of the lower dental arch to the upper dental arch or the second relative position of the lower dental arch to the upper dental arch; and receiving a user selection of the first relative position of the lower dental arch.

A 22$^{nd}$ implementation may further extend the 21$^{st}$ implementation. In the 22$^{nd}$ implementation, the method further comprises: discarding the second subset of the intraoral scan data.

A 23$^{rd}$ implementation may further extend the 21$^{st}$ implementation. In the 23$^{rd}$ implementation, the method further comprises: adjusting the second subset of the intraoral scan data to have the first relative position of the lower dental arch to the upper dental arch.

A 24$^{th}$ implementation may further extend any of the 21$^{st}$ through 23$^{rd}$ implementations. In the 24$^{th}$ implementation, the method further comprises: prompting a user to rescan a region of the bite of the patient associated with the second subset of the intraoral scan data.

A 25$^{th}$ implementation may further extend any of the 20$^{th}$ through 24$^{th}$ implementations. In the 25$^{th}$ implementation, the method further comprises: averaging the first relative position of the lower dental arch to the upper dental arch from the first subset of the intraoral scan data and the second relative position of the lower dental arch to the upper dental arch from the second subset of the intraoral scan data.

A 26$^{th}$ implementation may further extend any of the 20$^{th}$ through 25$^{th}$ implementations. In the 26$^{th}$ implementation, the method further comprises: generating a multi-bite solution comprising the first relative position of the lower dental arch to the upper dental arch and the second relative position of the lower dental arch to the upper dental arch.

A 27$^{th}$ implementation may further extend any of the 9$^{th}$ through 26$^{th}$ implementations. In the 27$^{th}$ implementation, performing the remedial action comprises prompting a user to rescan a portion of the bite of the patient.

A 28$^{th}$ implementation may further extend any of the 9$^{th}$ through 27$^{th}$ implementations. In the 28$^{th}$ implementation, a computer readable medium comprises instructions that, when executed by a processing device, cause the processing device to perform the method of any of the 9$^{th}$ through 27$^{th}$ implementations.

A 29$^{th}$ implementation may further extend any of the 20$^{th}$ through 27$^{th}$ implementations. In the 29$^{th}$ implementation, a system comprises: the intraoral scanner; and a computing device connected to the intraoral scanner via a wired or wireless connection, the computing device to perform the method of any of the 9$^{th}$ through 27$^{th}$ implementations.

In a 30$^{th}$ implementation, an intraoral scanning system comprises: an intraoral scanner configured to generate intraoral scan data of an upper dental arch of a patient, of a lower dental arch of the patient, and of a bite of the patient; and a computing device to receive the intraoral scan data from the intraoral scanner, wherein for scanning of the bite of the patient by the intraoral scanner the computing device is to output a sequence of instructions comprising: instructions for the patient to close their jaw prior to insertion of the intraoral scanner into the oral cavity; instructions for a dental practitioner to retract a left cheek of the patient and insert the intraoral scanner between the left cheek and the closed jaw; instructions for the dental practitioner to scan a left side of the upper dental arch and the lower dental arch while the patient's jaw remains closed; instructions for the dental practitioner to remove the intraoral scanner from the left cheek while the patient's jaw remains closed; instructions for the dental practitioner to retract a right cheek of the patient and insert the intraoral scanner between the right cheek and the closed jaw; and instructions for the dental practitioner to scan a right side of the upper dental arch and the lower dental arch while the patient's jaw remains closed; wherein the intraoral scan data of the bite of the patient received from the intraoral scanner was generated based on the dental practitioner following the sequence of instructions.

A 31$^{st}$ implementation may further extend the 30$^{th}$ implementation. In the 31$^{st}$ implementation, the computing device is further to: generate a first 3D model of the upper dental arch based on intraoral scans captured during scanning of the upper dental arch; generate a second 3D model of the lower dental arch based on intraoral scans captured during scanning of the lower dental arch; and determine a relative position and orientation of the first 3D model of the upper dental arch to the second 3D model of the lower dental arch based on intraoral scans captured during scanning of the bite of the patient.

A 32$^{nd}$ implementation may further extend the 30$^{th}$ or 31$^{st}$ implementation. In the 32$^{nd}$ implementation, the left cheek and the right cheek are retracted using a cheek retraction tool.

A 33$^{rd}$ implementation may further extend the 30$^{th}$ or 31$^{st}$ implementation. In the 33$^{rd}$ implementation, the left cheek and the right cheek are retracted using the intraoral scanner.

A 34$^{th}$ implementation may further extend any of the 30$^{th}$ through 33$^{rd}$ implementations. In the 34$^{th}$ implementation, the computing device is further to: determine whether the lower dental arch moved relative to the upper dental arch by more than a threshold amount during scanning of the bite of the patient; and perform one or more remedial actions responsive to determining that the lower dental arch moved relative to the upper dental arch by more than the threshold amount.

In a 35$^{th}$ implementation, an intraoral scanning system comprises: an intraoral scanner configured to generate intraoral scan data of an upper dental arch of a patient, of a lower dental arch of the patient, and of a bite of the patient; and a computing device to receive the intraoral scan data from the intraoral scanner, wherein for scanning of the bite of the patient by the intraoral scanner the computing device is to output a sequence of instructions comprising: instructions to retract a left cheek of the patient and to insert a first sleeve for the intraoral scanner between the left cheek and a jaw of the patient; instructions to retract a right cheek of the patient and insert a second sleeve for the intraoral scanner between the right cheek and the jaw of the patient; and instructions to perform the following while the jaw remains closed: insert the intraoral scanner into the first sleeve; scan a left side of the upper dental arch and the lower dental arch; remove the intraoral scanner from the first sleeve and from the left cheek; insert the intraoral scanner into the second sleeve; and scan a right side of the upper dental arch and the lower dental arch; wherein the intraoral scan data of the bite of the patient received from the intraoral scanner was generated based on a dental practitioner following the sequence of instructions A 36$^{th}$ implementation may further extend the 35$^{th}$ implementation. In the 36$^{th}$ implementation, the computing device is further to: generate a first 3D model of the upper dental arch based on intraoral scans captured during scanning of the upper dental arch; generate a second 3D model of the lower dental arch based on intraoral scans captured during scanning of the lower dental arch; and determine a relative position and orientation of the first 3D model of the upper dental arch to the second 3D model of the lower dental arch based on intraoral scans captured during scanning of the bite of the patient.

A 37$^{th}$ implementation may further extend the 35$^{th}$ or 36$^{th}$ implementation. In the 37$^{th}$ implementation, the computing device is further to: determine whether the lower dental arch moved relative to the upper dental arch by more than a threshold amount during scanning of the bite of the patient; and perform one or more remedial actions responsive to determining that the lower dental arch moved relative to the upper dental arch by more than the threshold amount.

BRIEF DESCRIPTION OF THE DRAWINGS

Embodiments of the present disclosure are illustrated by way of example, and not by way of limitation, in the figures of the accompanying drawings.

DETAILED DESCRIPTION

Figure 1A:
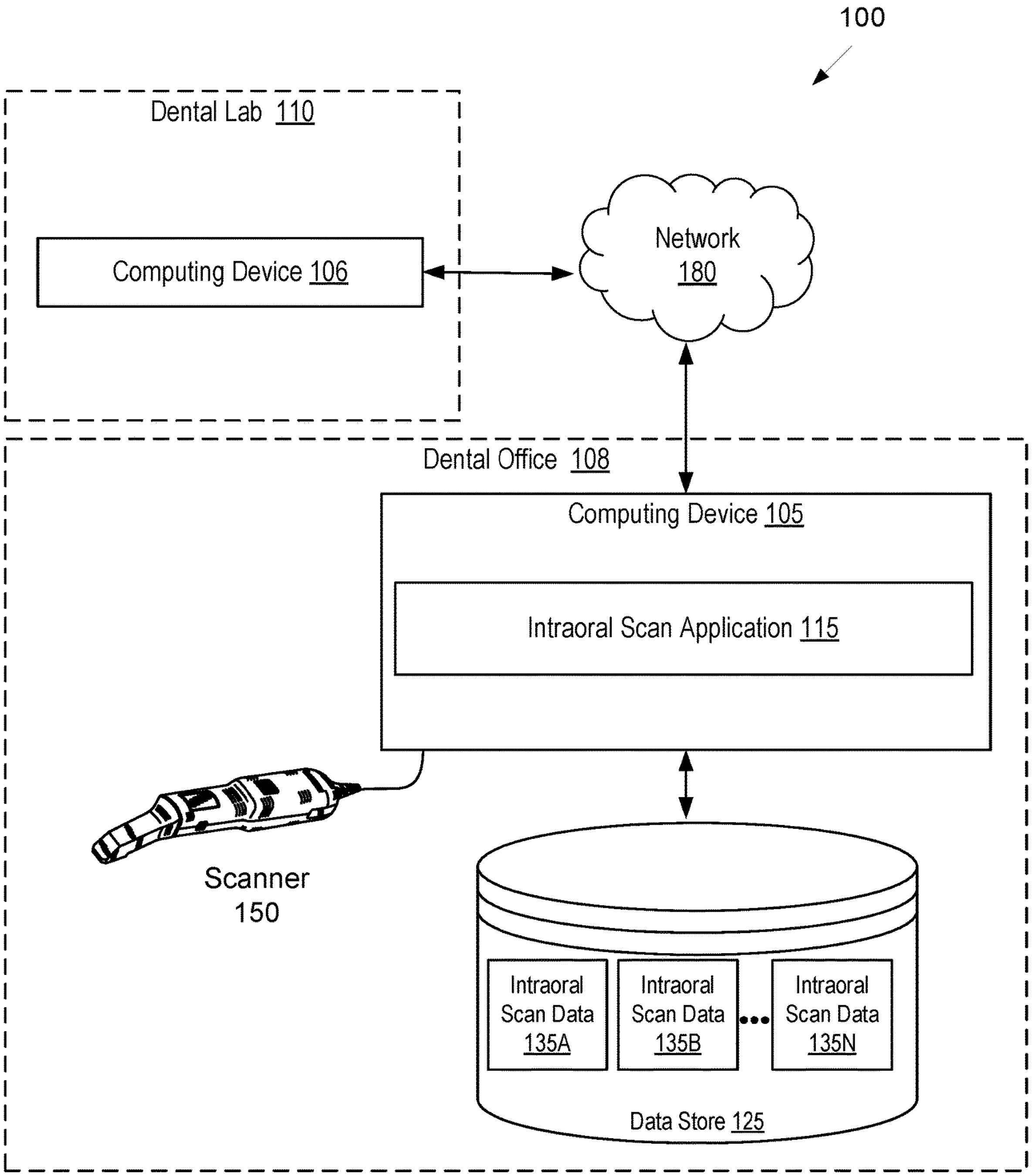
FIG. 1A illustrates one embodiment of a system for performing intraoral scanning and/or generating a virtual three-dimensional model of an intraoral site.

Described herein are methods and systems for performing intraoral scanning of a patient bite, and for assessing intraoral scans and/or images captured during scanning of a patient bite. In some embodiments, techniques or protocols for scanning a patient bite are implemented that improve a quality of final virtual three-dimensional (3D) models of the patient's dental arches. Also described are intraoral scanning systems that guide a user of the intraoral scanning system (e.g., such as a dental practitioner) to perform intraoral scanning of a patient bite using one or more specific scanning techniques to improve the quality and accuracy of the scans of the patient bite.

A major contributor to inaccuracies of 3D models of dental arches generated from intraoral scanning is the scan of the patient bite. Traditionally, the bite scan protocol across the industry is to have a patient open their mouth, insert an intraoral scanner into a first side (e.g., right side) of the mouth between the patient's jaw and cheek with the mouth open, have the patient close their mouth with the intraoral scanner inserted, and then generate intraoral scans of a first side of the patient's jaw. This process is then repeated for the second side (e.g., left side) of the patient's mouth, where the patient again opens their mouth, the intraoral scanner is inserted into a second side of the mouth between the patient's jaw and cheek with the mouth open, the patient closes their mouth with the intraoral scanner inserted, and intraoral scans of a second side of the patient's jaw are generated.

Internal research has shown that the repeated opening and closing of the mouth during bite scanning causes the poor bite registration as well as poor repeatability, where bite registration includes the determination of the relative position and/or orientation of the lower dental arch to the upper dental arch. Accordingly, if the same patient is scanned using this patient bite scan protocol multiple times, each repetition is likely to yield different results. Tests have shown differences in the bite registration that are greater than 300 microns when a traditional bite scan protocol is used. A poor bite registration results in poor or low quality occlusal contact information between teeth of the upper dental arch and teeth of the lower dental arch. Such low quality occlusal contact information can cause dental prosthetics such as crowns, bridges, and so on to have a poor occlusal fit. If a dental prosthetic has poor occlusal fit, then either a doctor needs to manually modify the dental prosthetic (e.g., such as by grinding the dental prosthetic to cause it to contact other teeth properly) or a new dental prosthetic needs to be manufactured. Both remedies increase an overall cost of the dental prosthetic, a time that a doctor spends preparing and fitting the dental prosthetic, and so on.

Embodiments provide multiple new bite scan protocols that, when implemented, significantly increase the accuracy and repeatability of a bite scan. In a first new bite scan protocol, a patient is directed to close their jaw prior to insertion of an intraoral scanner into the oral cavity of the patient. A doctor then retracts a left (or right) cheek of the patient and inserts an intraoral scanner between the left (or right) cheek and the patient's closed jaw. Alternatively, the intraoral scanner may be inserted while the patient's jaw is open, and the patient may close their jaw after insertion of the intraoral scanner on the left (or right) side. The left (or right) side of the upper and lower dental arches are then scanned while the patient's jaw remains closed to capture the relation of the upper and lower dental arches from the left (or right) side. The intraoral scanner is then removed from the patient's mouth while the patient's jaw remains closed. The doctor retracts the right (or left) cheek of the patient and inserts the intraoral scanner between the right (or left) cheek and the patient's closed jaw. The right (or left) side of the upper and lower dental arches are then scanned while the patient's jaw remains closed to capture the relation of the upper and lower dental arches from the right (or left) side. Because the patient's jaw remains closed and the lower jaw does not move relative to the upper jaw during the bite scan process, the relation between the upper and lower dental arches as determined from the left side scans/images is very close if not the same as the relation between the upper and lower dental arches as determined from the right side scans/images. This results in an improved bite registration and high quality occlusal contact information. A computing device of an intraoral scanning system may output a sequence of instructions for performing this new bite scan protocol before and/or during scanning of a patient bite in embodiments. For example, such instructions may be output to a display of the computing device.

In a second new bite scan protocol, a patient's left cheek is retracted and a first sleeve of an intraoral scanner is inserted between the left cheek of the patient and the patient's jaw, which may be an open or closed jaw. Similarly, the patient's right cheek is retracted and a second sleeve of the intraoral scanner is inserted between the right cheek of the patient and the patient's jaw, which may be an open or closed jaw. The jaw may then close, or may have already been closed. The intraoral scanner is inserted into the first (or second) sleeve while the patient's jaw remains closed. The left (or right) side of the upper and lower dental arches are then scanned while the patient's jaw remains closed to capture the relation of the upper and lower dental arches from the left (or right) side. The intraoral scanner is then removed from the first (or second) sleeve and from the left (or right) cheek while the patient's jaw remains closed. The intraoral scanner is inserted into the second (or first) sleeve while the patient's jaw remains closed. The right (or left) side of the upper and lower dental arches are then scanned while the patient's jaw remains closed to capture the relation of the upper and lower dental arches from the right (or left) side. Because the patient's jaw remains closed and the lower jaw does not move relative to the upper jaw during the bite scan process, the relation between the upper and lower dental arches as determined from the left side scans/images is very close if not the same as the relation between the upper and lower dental arches as determined from the right side scans/images. This results in an improved bite registration and high quality occlusal contact information. A computing device of an intraoral scanning system may output a sequence of instructions for performing this new bite scan protocol before and/or during scanning of a patient bite in embodiments. For example, such instructions may be output to a display of the computing device.

Regardless of the bite scan protocol that is used to perform a bite scan, it can be beneficial to assess the amount of movement of the lower jaw and dental arch relative to the upper jaw and dental arch during the bite scan process. A determination of an amount of movement that is over a threshold level can indicate that a bite registration will be of low quality and/or will be unacceptable. A determination of an amount of movement that is below a threshold level can indicate that a bite registration will be of high quality and/or will be acceptable. Various techniques for determining a relative position and/or orientation of a lower dental arch to an upper dental arch and of identifying movement of the lower jaw and/or changes in the relative position and/or orientation of the lower dental arch to the upper dental arch are described herein. Such techniques may be applied to assess a quality of a bite registration and to determine whether one or more remedial actions should be performed after a bite scan. Such remedial actions may include outputting a warning, recommending a rescan of one or more portions of a patient's bite (e.g., rescanning a left side of the upper and lower dental arch with the jaw closed and/or a right side of the upper and lower dental arch with the jaw closed), and so on.

The techniques, methods, protocols and systems described in embodiments provide 3D models of dental arches to be generated with increased accuracy, and in particular with increased accuracy with regards to occlusal contact information. Such increased accuracy may improve the quality of dental prosthetics and reduce an amount of rework and replacement of prosthetics that are manufactured.

Various embodiments are described herein. It should be understood that these various embodiments may be implemented as stand-alone solutions and/or may be combined. Accordingly, references to an embodiment, or one embodiment, may refer to the same embodiment and/or to different embodiments. Additionally, some embodiments are discussed with reference to restorative dentistry. However, it should be understood that embodiments discussed with reference to restorative dentistry (e.g., prosthodontics) may also apply to corrective dentistry (e.g., orthodontia).

Some embodiments are discussed herein with reference to intraoral scans and intraoral images. However, it should be understood that embodiments described with reference to intraoral scans also apply to lab scans or model/impression scans. A lab scan or model/impression scan may include one or more images of a dental site or of a model or impression of a dental site, which may or may not include height maps, and which may or may not include color images.

FIG. 1A illustrates one embodiment of a system 100 for performing intraoral scanning and/or generating a virtual three-dimensional model of an intraoral site. System 100 includes a dental office 108 and optionally one or more dental lab 110. The dental office 108 and the dental lab 110 each include a computing device 105, 106, where the computing devices 105, 106 may be connected to one another via a network 180. The network 180 may be a local area network (LAN), a public wide area network (WAN) (e.g., the Internet), a private WAN (e.g., an intranet), or a combination thereof.

Computing device 105 may be coupled to one or more intraoral scanner 150 (also referred to as a scanner) and/or a data store 125 via a wired or wireless connection. In one embodiment, multiple scanners 150 in dental office 108 wirelessly connect to computing device 105. In one embodiment, scanner 150 is wirelessly connected to computing device 105 via a direct wireless connection. In one embodiment, scanner 150 is wirelessly connected to computing device 105 via a wireless network. In one embodiment, the wireless network is a Wi-Fi network. In one embodiment, the wireless network is a Bluetooth network, a Zigbee network, or some other wireless network. In one embodiment, the wireless network is a wireless mesh network, examples of which include a Wi-Fi mesh network, a Zigbee mesh network, and so on. In an example, computing device 105 may be physically connected to one or more wireless access points and/or wireless routers (e.g., Wi-Fi access points/routers). Intraoral scanner 150 may include a wireless module such as a Wi-Fi module, and via the wireless module may join the wireless network via the wireless access point/router. Computing device 106 may also be connected to a data store (not shown). The data stores may be local data stores and/or remote data stores. Computing device 105 and computing device 106 may each include one or more processing devices, memory, secondary storage, one or more input devices (e.g., such as a keyboard, mouse, tablet, touchscreen, microphone, camera, and so on), one or more output devices (e.g., a display, printer, touchscreen, speakers, etc.), and/or other hardware components.

In embodiments, scanner 150 includes an inertial measurement unit (IMU). The IMU may include an accelerometer, a gyroscope, a magnetometer, a pressure sensor and/or other sensor. For example, scanner 150 may include one or more micro-electromechanical system (MEMS) IMU. The IMU may generate inertial measurement data, including acceleration data, rotation data, and so on.

Computing device 105 and/or data store 125 may be located at dental office 108 (as shown), at dental lab 110, or at one or more other locations such as a server farm that provides a cloud computing service. Computing device 105 and/or data store 125 may connect to components that are at a same or a different location from computing device 105 (e.g., components at a second location that is remote from the dental office 108, such as a server farm that provides a cloud computing service). For example, computing device 105 may be connected to a remote server, where some operations of intraoral scan application 115 are performed on computing device 105 and some operations of intraoral scan application 115 are performed on the remote server.

Some additional computing devices may be physically connected to the computing device 105 via a wired connection. Some additional computing devices may be wirelessly connected to computing device 105 via a wireless connection, which may be a direct wireless connection or a wireless connection via a wireless network. In embodiments, one or more additional computing devices may be mobile computing devices such as laptops, notebook computers, tablet computers, mobile phones, portable game consoles, and so on. In embodiments, one or more additional computing devices may be traditionally stationary computing devices, such as desktop computers, set top boxes, game consoles, and so on. The additional computing devices may act as thin clients to the computing device 105. In one embodiment, the additional computing devices access computing device 105 using remote desktop protocol (RDP). In one embodiment, the additional computing devices access computing device 105 using virtual network control (VNC). Some additional computing devices may be passive clients that do not have control over computing device 105 and that receive a visualization of a user interface of intraoral scan application 115. In one embodiment, one or more additional computing devices may operate in a master mode and computing device 105 may operate in a slave mode.

Intraoral scanner 150 may be a wand and/or include a probe (e.g., a hand held probe) for optically capturing three-dimensional structures. The intraoral scanner 150 may be used to perform an intraoral scan of a patient's oral cavity. An intraoral scan application 115 running on computing device 105 may communicate with the scanner 150 to effectuate the intraoral scan. A result of the intraoral scan may be intraoral scan data 135A, 135B through 135N that may include one or more sets of intraoral scans and/or intraoral images. Each intraoral scan may include a two-dimensional (2D) or 3D image or point cloud that may include depth information (e.g., a height map) of a portion of a dental site. In embodiments, intraoral scans include x, y and z information. In one embodiment, the intraoral scanner 150 generates numerous discrete (i.e., individual) intraoral scans.

In some embodiments, sets of discrete intraoral scans are merged into a smaller set of blended intraoral scans, where each blended scan is a combination of multiple discrete scans. The intraoral scan data 135A-N may include raw scans and/or blended scans, each of which may be referred to as intraoral scans (and in some instances as intraoral images). While scanning, the intraoral scanner may generate multiple (e.g., tens) of scans per second (referred to as raw scans). In order to improve the quality of the data captured, a blending process may be used to combine a sequence of raw scans into a blended scan by some averaging process. Additionally, intraoral scanner 150 may generate many scans per second. Groups of similar scans may be combined into the blended scans, and the blended scans may be processed as a unit. This may vastly reduce the computation resources used to process the intraoral scans without degrading quality. In one embodiment, each blended scan includes data from up to 20 raw scans, and further includes scans that differ by less than a threshold angular difference from one another and/or by less than a threshold positional difference from one another. Accordingly, some blended scans may include data from 20 scans, while other blended scans may include data from fewer than 20 scans.

Intraoral scan data 135A-N may also include color 2D images and/or images of particular wavelengths (e.g., near-infrared (NIRI) images, infrared images, ultraviolet images, etc.) of a dental site in embodiments. In embodiments, intraoral scanner 150 alternates between generation of 3D intraoral scans and one or more types of 2D intraoral images (e.g., color images, NIRI images, etc.) during scanning. For example, one or more 2D color images may be generated between generation of a fourth and fifth intraoral scan. For example, some scanners may include multiple image sensors that generate different 2D color images of different regions of a patient's dental arch concurrently. These 2D color images may be stitched together to form a single color representation of a larger field of view that includes a combination of the fields of view of the multiple image sensors.

The scanner 150 may transmit the intraoral scan data 135A, 135B through 135N to the computing device 105. Computing device 105 may store the intraoral scan data 135A-135N in data store 125.

According to an example, a user (e.g., a practitioner) may subject a patient to intraoral scanning. In doing so, the user may apply scanner 150 to one or more patient intraoral locations. The scanning may be divided into one or more segments (also referred to as roles). As an example, the segments may include a lower dental arch of the patient, an upper dental arch of the patient, one or more preparation teeth of the patient (e.g., teeth of the patient to which a dental device such as a crown or other dental prosthetic will be applied), one or more teeth which are contacts of preparation teeth (e.g., teeth not themselves subject to a dental device but which are located next to one or more such teeth or which interface with one or more such teeth upon mouth closure), and/or patient bite (e.g., scanning performed with closure of the patient's mouth with the scan being directed towards an interface area of the patient's upper and lower teeth). Via such scanner application, the scanner 150 may provide intraoral scan data 135A-N to computing device 105. The intraoral scan data 135A-N may be provided in the form of intraoral scan data sets, each of which may include 2D intraoral images (e.g., color 2D images) and/or 3D intraoral scans of particular teeth and/or regions of an intraoral site. In one embodiment, separate intraoral scan data sets are created for the maxillary arch, for the mandibular arch, for a patient bite, and/or for each preparation tooth. Alternatively, a single large intraoral scan data set is generated (e.g., for a mandibular and/or maxillary arch). Intraoral scans may be provided from the scanner 150 to the computing device 105 in the form of one or more points (e.g., one or more pixels and/or groups of pixels). For instance, the scanner 150 may provide an intraoral scan as one or more point clouds. The intraoral scans may each comprise height information (e.g., a height map that indicates a depth for each pixel).

The manner in which the oral cavity of a patient is to be scanned may depend on the procedure to be applied thereto. For example, if an upper or lower denture is to be created, then a full scan of the mandibular or maxillary edentulous arches may be performed. In contrast, if a bridge is to be created, then just a portion of a total arch may be scanned which includes an edentulous region, the neighboring preparation teeth (e.g., abutment teeth) and the opposing arch and dentition. Alternatively, full scans of upper and/or lower dental arches may be performed if a bridge is to be created.

By way of non-limiting example, dental procedures may be broadly divided into prosthodontic (restorative) and orthodontic procedures, and then further subdivided into specific forms of these procedures. Additionally, dental procedures may include identification and treatment of gum disease, sleep apnea, and intraoral conditions. The term prosthodontic procedure refers, inter alia, to any procedure involving the oral cavity and directed to the design, manufacture or installation of a dental prosthesis at a dental site within the oral cavity (intraoral site), or a real or virtual model thereof, or directed to the design and preparation of the intraoral site to receive such a prosthesis. A prosthesis may include any restoration such as crowns, veneers, inlays, onlays, implants and bridges, for example, and any other artificial partial or complete denture. The term orthodontic procedure refers, inter alia, to any procedure involving the oral cavity and directed to the design, manufacture or installation of orthodontic elements at a intraoral site within the oral cavity, or a real or virtual model thereof, or directed to the design and preparation of the intraoral site to receive such orthodontic elements. These elements may be appliances including but not limited to brackets and wires, retainers, clear aligners, or functional appliances.

In embodiments, intraoral scanning may be performed on a patient's oral cavity during a visitation of dental office 108. The intraoral scanning may be performed, for example, as part of a semi-annual or annual dental health checkup. The intraoral scanning may also be performed before, during and/or after one or more dental treatments, such as orthodontic treatment and/or prosthodontic treatment. The intraoral scanning may be a full or partial scan of the upper and/or lower dental arches, and may be performed in order to gather information for performing dental diagnostics, to generate a treatment plan, to determine progress of a treatment plan, and/or for other purposes. The dental information (intraoral scan data 135A-N) generated from the intraoral scanning may include 3D scan data, 2D color images, NIRI and/or infrared images, and/or ultraviolet images, of all or a portion of the upper jaw and/or lower jaw. The intraoral scan data 135A-N may further include one or more intraoral scans showing a relationship of the upper dental arch to the lower dental arch. These intraoral scans may be usable to determine a patient bite and/or to determine occlusal contact information for the patient. The patient bite may include determined relationships between teeth in the upper dental arch and teeth in the lower dental arch.

For many prosthodontic procedures (e.g., to create a crown, bridge, veneer, etc.), an existing tooth of a patient is ground down to a stump. The ground tooth is referred to herein as a preparation tooth, or simply a preparation. The preparation tooth has a margin line (also referred to as a finish line), which is a border between a natural (unground) portion of the preparation tooth and the prepared (ground) portion of the preparation tooth. The preparation tooth is typically created so that a crown or other prosthesis can be mounted or seated on the preparation tooth. In many instances, the margin line of the preparation tooth is subgingival (below the gum line).

After a preparation tooth is created, a practitioner typically performs operations to ready that preparation tooth for scanning. Readying the preparation tooth for scanning may include wiping blood, saliva, etc. off of the preparation tooth and/or separating a patient's gum from the preparation tooth to expose the finish line. In some instances, a practitioner will insert a cord (also referred to as a dental wire) around the preparation tooth between the preparation tooth and the patient's gum. The practitioner will then remove the cord before generating a set of intraoral scans of the preparation tooth. The soft tissue of the gum will then revert back to its natural position, and in many cases collapses back over the finish line, after a brief time period.

Intraoral scanners may work by moving the scanner 150 inside a patient's mouth to capture all viewpoints of one or more tooth. During scanning, the scanner 150 is calculating distances to solid surfaces in some embodiments. These distances may be recorded as images called 'height maps'. Each scan is overlapped algorithmically, or 'stitched', with the previous set of scans to generate a growing 3D surface. As such, each scan is associated with a rotation in space, or a projection, to how it fits into the 3D surface.

During intraoral scanning, intraoral scan application 115 may register and stitch together two or more intraoral scans generated thus far from the intraoral scan session and/or from scanning of a current segment (e.g., upper dental arch, lower dental arch, or patient bite). In one embodiment, performing registration includes capturing 3D data of various points of a surface in multiple scans, and registering the scans by computing transformations between the scans. One or more 3D surfaces may be generated based on the registered and stitched together intraoral scans during the intraoral scanning. The one or more 3D surfaces may be output to a display so that a doctor or technician can view their scan progress thus far. As each new intraoral scan is captured and registered to previous intraoral scans and/or a 3D surface, the one or more 3D surfaces may be updated, and the updated 3D surface(s) may be output to the display. In embodiments, separate 3D surfaces are generated for the upper jaw and the lower jaw. This process may be performed in real time or near-real time to provide an updated view of the captured 3D surfaces during the intraoral scanning process.

When a scan session or a portion of a scan session associated with a particular scanning role (e.g., upper jaw role, lower jaw role, bite role, etc.) is complete (e.g., all scans for an intraoral site or dental site have been captured), intraoral scan application 115 may automatically generate a virtual 3D model of one or more scanned dental sites (e.g., of an upper jaw and a lower jaw). The final 3D model may be a set of 3D points and their connections with each other (i.e. a mesh). To generate the virtual 3D model, intraoral scan application 115 may register and stitch together the intraoral scans generated from the intraoral scan session that are associated with a particular scanning role. The registration performed at this stage may be more accurate than the registration performed during the capturing of the intraoral scans, and may take more time to complete than the registration performed during the capturing of the intraoral scans. In one embodiment, performing scan registration includes capturing 3D data of various points of a surface in multiple scans, and registering the scans by computing transformations between the scans. The 3D data may be projected into a 3D space of a 3D model to form a portion of the 3D model. The intraoral scans may be integrated into a common reference frame by applying appropriate transformations to points of each registered scan and projecting each scan into the 3D space.

In one embodiment, registration is performed for adjacent or overlapping intraoral scans (e.g., each successive frame of an intraoral video). In one embodiment, registration is performed using blended scans. Registration algorithms are carried out to register two adjacent or overlapping intraoral scans (e.g., two adjacent blended intraoral scans) and/or to register an intraoral scan with a 3D model, which essentially involves determination of the transformations which align one scan with the other scan and/or with the 3D model. Registration may involve identifying multiple points in each scan (e.g., point clouds) of a scan pair (or of a scan and the 3D model), surface fitting to the points, and using local searches around points to match points of the two scans (or of the scan and the 3D model). For example, intraoral scan application 115 may match points of one scan with the closest points interpolated on the surface of another scan, and iteratively minimize the distance between matched points. Other registration techniques may also be used.

Intraoral scan application 115 may repeat registration for all intraoral scans of a sequence of intraoral scans (e.g., generated during a particular scanning role) to obtain transformations for each intraoral scan, to register each intraoral scan with previous intraoral scan(s) and/or with a common reference frame (e.g., with the 3D model). Intraoral scan application 115 may integrate intraoral scans into a single virtual 3D model by applying the appropriate determined transformations to each of the intraoral scans. Each transformation may include rotations about one to three axes and translations within one to three planes.

Intraoral scans may be assigned weights based on scores assigned to those scans. Assigned weights may be associated with different dental sites. In one embodiment, a weight may be assigned to each scan (e.g., to each blended scan) for a dental site (or for multiple dental sites). During model generation, conflicting data from multiple intraoral scans may be combined using a weighted average to depict a dental site. The weights that are applied may be those weights that were assigned based on quality scores for the dental site. For example, processing logic may determine that data for a particular overlapping region from a first set of intraoral scans is superior in quality to data for the particular overlapping region of a second set of intraoral scans. The first intraoral scan data set may then be weighted more heavily than the second intraoral scan data set when averaging the differences between the intraoral scan data sets. For example, the first intraoral scans assigned the higher rating may be assigned a weight of 70% and the second intraoral scans may be assigned a weight of 30%. Thus, when the data is averaged, the merged result will look more like the depiction from the first intraoral scan data set and less like the depiction from the second intraoral scan data set.

Intraoral scan application 115 may generate one or more 3D models from intraoral scans, and may display the 3D models to a user (e.g., a doctor) via a user interface. Intraoral scans generated during scanning of a patient bite may then be used to determine the relative position and/or orientation of the 3D model of the patient's lower dental arch to the 3D model of the patient's upper dental arch. In embodiments, the relative position of the lower dental arch to the upper dental arch has a position accuracy of smaller than 500 microns and an angular accuracy of smaller than 10 milliradian. The 3D models can be checked visually by the doctor. The doctor can virtually manipulate the 3D models via the user interface with respect to up to six degrees of freedom (i.e., translated and/or rotated with respect to one or more of three mutually orthogonal axes) using suitable user controls (hardware and/or virtual) to enable viewing of the 3D model(s) from any desired direction. The doctor may review (e.g., visually inspect) the generated 3D model(s) of an intraoral site and determine whether the 3D model(s) are acceptable.

Figure 1B:
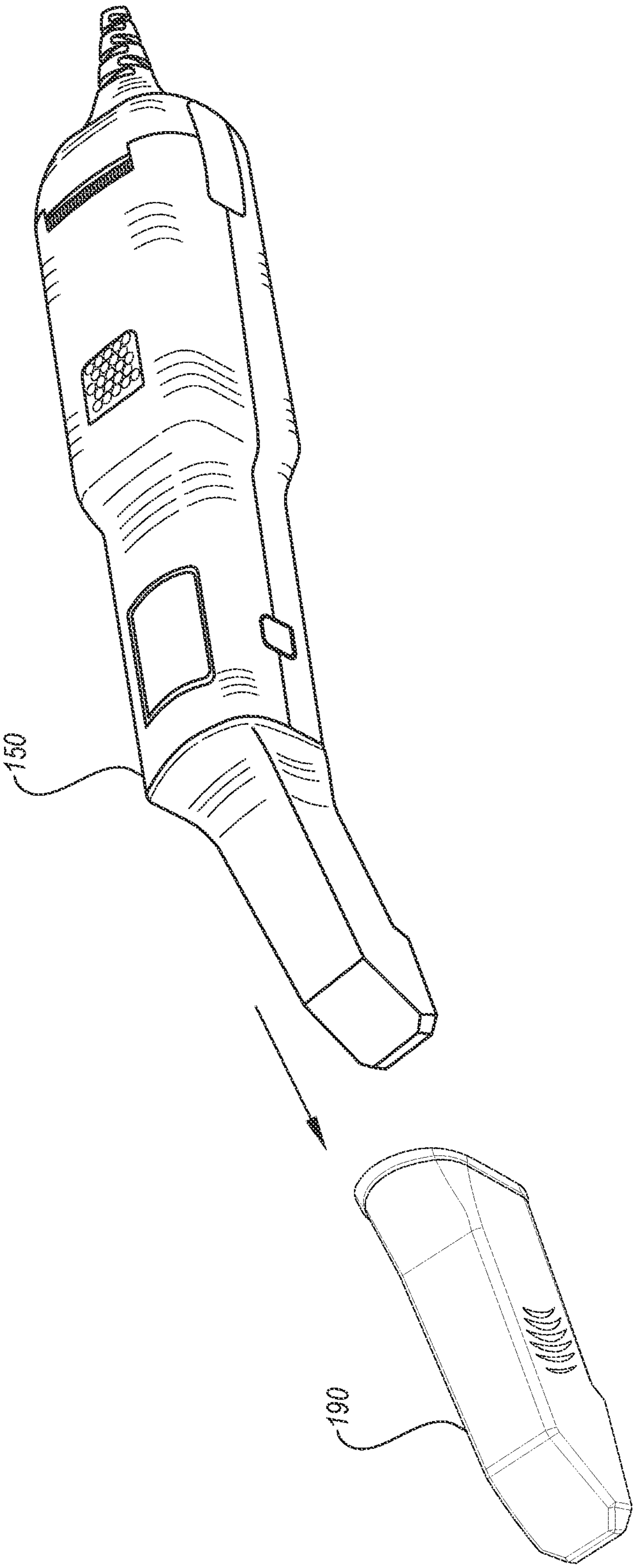
FIG. 1B illustrates an intraoral scanner and a protective sleeve for the intraoral scanner, in accordance with embodiments of the present disclosure.

FIG. 1B illustrates an intraoral scanner 150 and a protective sleeve 190 for the intraoral scanner, in accordance with embodiments of the present disclosure. The intraoral scanner 150 may be exposed to fluids of a patient's mouth, which may contaminate the intraoral scanner 150. Accordingly, in some embodiments a probe of the intraoral scanner 150 is inserted into protective sleeve 190. Protective sleeve 190 may include a window (not shown) that aligns with a window or opening in a head of the intraoral scanner. Accordingly, light may pass through the protective sleeve and into and out of the intraoral scanner to generate scans and images. The protective sleeve may protect the intraoral scanner from contact with a patient's oral cavity, enabling the intraoral scanner to be used on multiple patients without cleansing the intraoral scanner in an autoclave between patients. Rather, a new protective sleeve may simply be used between patients. As shown, the probe of the intraoral scanner 150 (including the head of the intraoral scanner) may be inserted into the protective sleeve 190 by moving the scanner 150 relative to the protective sleeve 190 along the indicated arrow.

The protective sleeve 190 may have a rigid or semi-rigid body that enables it to maintain its shape even while it is not installed on an intraoral scanner. This feature may be taken advantage of in embodiments to enable multiple protective sleeves to be inserted into different regions of a patient's mouth, and for those different regions of the patient's mouth to be scanned without the patient having to open their mouth between scanning of the different regions, as is discussed in greater detail below with reference to FIG. 3. The protective sleeve 190 may be disposable or reusable. In embodiments, the protective sleeve may be made of plastic, rubber, and/or other materials.

FIGS. 2A-8 are flow charts illustrating various methods that may be performed to implement improved scanning of a patient bite, which may increase an accuracy of 3D models of dental arches and of manufactured prosthodontics. Some methods may be performed by a doctor or technician performing an intraoral scan using an intraoral scanner. Some methods may be performed by a processing logic that may comprise hardware (e.g., circuitry, dedicated logic, programmable logic, microcode, etc.), software (e.g., instructions run on a processing device to perform hardware simulation), firmware, or a combination thereof. In one embodiment, at least some operations of the methods are performed by a computing device of a scanning system and/or by a server computing device (e.g., by computing device 105 of FIG. 1 or computing device 1100 of FIG. 11).

Figure 2A:
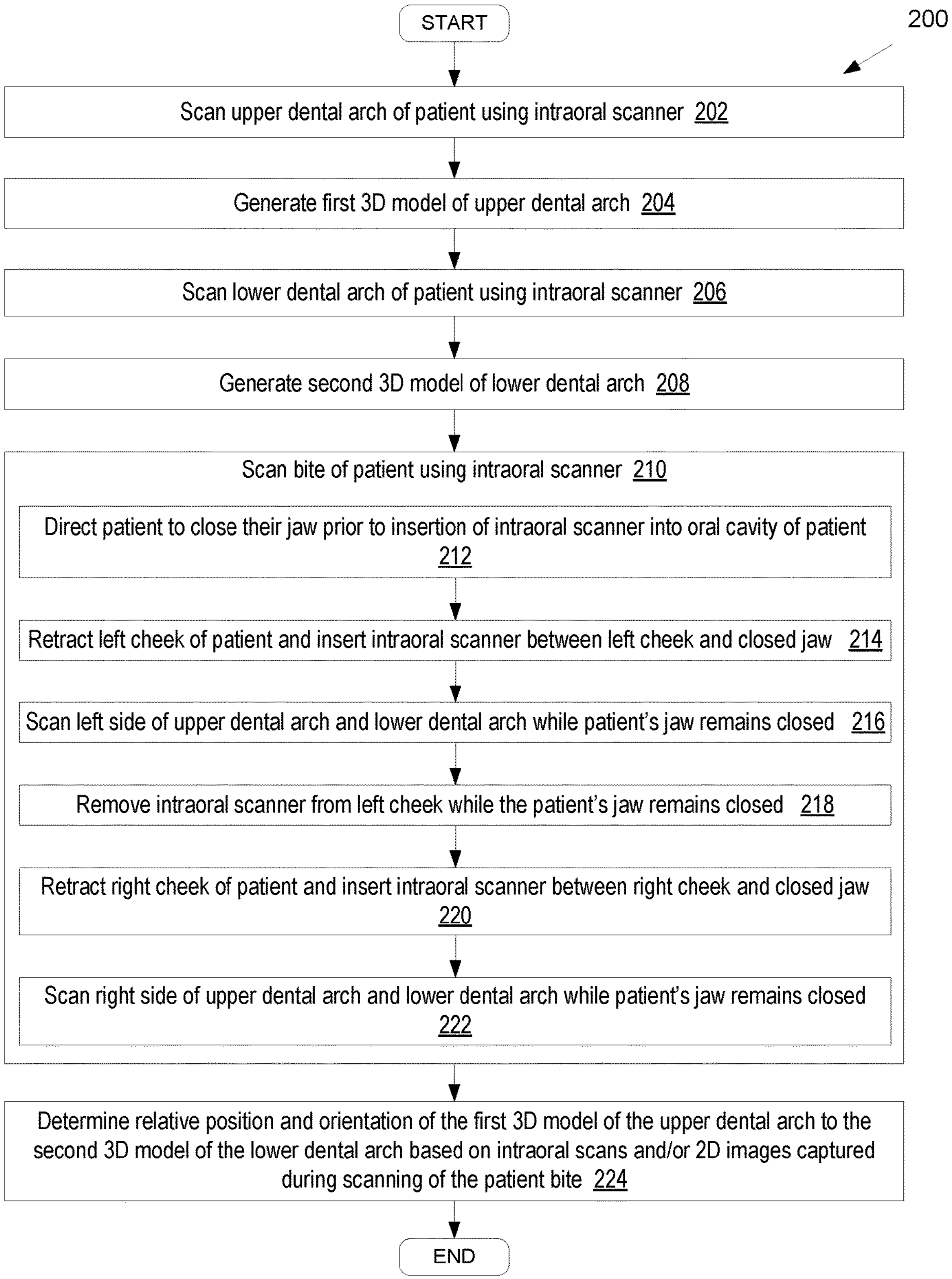
FIG. 2A is a flow chart illustrating an embodiment for a method of scanning a patient bite using an intraoral scanner.

FIG. 2A is a flow chart illustrating an embodiment for a method 200 of scanning a patient bite using an intraoral scanner. At block 202 of method 200, a practitioner (e.g., a doctor, dentist, dental technician, etc.) scans an upper dental arch of a patient using an intraoral scanner to generate a first set of intraoral scan data of the upper dental arch. At block 204, processing logic may generate a first 3D model of the upper dental arch using the first set of intraoral scan data generated from scanning of the upper dental arch. At block 206, the practitioner scans a lower dental arch of the patient using the intraoral scanner to generate a second set of intraoral scan data of the lower dental arch. At block 208, processing logic may generate a second 3D model of the lower dental arch using the second set of intraoral scan data generated from scanning of the lower dental arch. Note that the upper and lower dental arch may be scanned in any order. In some embodiments, the practitioner provides an indication that they are scanning the upper dental arch prior to or after scanning the upper dental arch, and similarly provides an indication that they are scanning the lower dental arch prior to or after scanning the lower dental arch. This may enable the system to identify the scans to use in generating the 3D model of the upper dental arch and the scans to use in generating the 3D model of the lower dental arch. In some embodiments, processing logic automatically determines whether an upper dental arch, lower dental arch, or patient bite is being scanned using one or more trained machine learning models. In some embodiments, processing logic automatically determines a scanning role (e.g., determines whether scans are of an upper dental arch, lower dental arch, or patient bite) using the techniques set forth in U.S. application Ser. No. 17/230,825, filed Apr. 14, 2021, entitled "Smart Scanning for Intraoral Scanners", which is incorporated by reference herein in its entirety.

At block 210, the practitioner scans a bite of the patient using the intraoral scanner. The bite of the patient may be scanned according to a particular bite scan protocol that improves an overall quality of a bite registration and of occlusal contact information in embodiments.

In one embodiment, at block 212 the practitioner directs the patient to close their jaw prior to insertion of the intraoral scanner into the oral cavity of the patient. In one embodiment, the patient is directed to swallow and to close their jaw after swallowing. This may cause the patient's lower jaw to achieve a natural closed position relative to the upper jaw. Alternatively, the patient may be directed to place their tongue against the top of their palette while they close their mouth, which can also achieve a natural closed position of the lower jaw. In one embodiment, at block 214 the practitioner retracts a first side of the patient's cheeks (e.g., the patient's left cheek) and inserts the intraoral scanner (e.g., the probe of the intraoral scanner) between the first side of the patient's cheeks (e.g., the left cheek) and the closed jaw of the patient. In one embodiment, the cheek is retracted using a specialized cheek retractor tool. The cheek retractor tool may retract the cheek in a manner that does not interfere with a scan or a tip of an intraoral scanner, and that does not impose a force that would cause the patient's jaw to move. Accordingly, the cheek retractor tool is not a part of a scanned area in embodiments. In one embodiment, the intraoral scanner is inserted into the patient's oral cavity while the patient's jaw is still opened, and the patient closes their jaw while the intraoral scanner is inserted between the first side of the patient's cheeks (e.g., left cheek) and the patient's jaw. In one embodiment, this process is performed while the patient swallows or immediately after the patient swallows.

At block 216, the practitioner scans a first side of the upper and lower dental arch (e.g., the left side of the patient's jaw) while the patient's jaw remains closed. This may produce a first set of intraoral scans and/or images that are usable to determine a relative position and/or orientation of the lower dental arch (e.g., the 3D model of the lower dental arch) to the upper dental arch (e.g., the 3D model of the upper dental arch). For accuracy, the other side of the patient's jaw may also be scanned to determine the relative position and/or orientation of the lower dental arch to the upper dental arch.

At block 218, the practitioner removes the intraoral scanner from first side of the cheeks (e.g., the left cheek) while the patient's jaw remains closed.

In one embodiment, at block 220 the practitioner retracts the second side of the patient's cheeks (e.g., the patient's right cheek) and inserts the intraoral scanner (e.g., the probe of the intraoral scanner) between the first side of the patient's cheeks (e.g., the right cheek) and the closed jaw of the patient. The patient's jaw may remain closed and in the same relative position during scanning of the left and right sides of the jaw.

At block 222, the practitioner scans the first side of the upper and lower dental arch (e.g., the right side of the patient's jaw) while the patient's jaw remains closed. This may produce a second set of intraoral scans and/or images that are usable to determine a relative position and/or orientation of the lower dental arch (e.g., the 3D model of the lower dental arch) to the upper dental arch (e.g., the 3D model of the upper dental arch). After scanning of the second side (e.g., the right side) of the patient's jaw, the intraoral scanner may be removed from the patient's oral cavity, and the patient may open their jaw. In some embodiments, the right side of the patient bite is scanned before the left side of the patient bite. In other embodiments, the left side of the patient bite is scanned before the right side of the patient bite.

In some instances, the practitioner may also scan a front, incisor region of the patient bite while the patient's jaw remains closed. This may produce a third set of intraoral scans and/or images that are usable to determine the relative position and/or orientation of the lower dental arch to the upper dental arch. The third set of intraoral scans and/or images can improve precision by providing more relative data between the upper and lower dental arches. In general the intraoral scanner exerts less force against the on the patient's jaw, lips, mouth, etc. than buccal scans generated while the jaw is closed (e.g., the left and right scans of the patient bite), and so should not cause the lower jaw to move relative to the upper jaw. In some instances, the scan of the front, incisor region is performed instead of the scan of one of the left side of the patient bite or the right side of the patient bite.

At block 224, processing logic determines a relative position and orientation of the upper dental arch to the lower dental arch and/or movement of the lower dental arch based on the intraoral scans and/or 2D images captured during scanning of the patient bite (e.g., based on the first set of intraoral scans and the second set of intraoral scans). The relative position and orientation of the upper dental arch and lower dental arch may be determined by registering a first region of the intraoral scans (e.g., a region depicting the upper dental arch) to the first 3D model of the upper dental arch and by registering a second region of the intraoral scans (e.g., a region depicting the lower dental arch) to the second 3D model of the lower dental arch. Due to the patient keeping their jaw closed and immobile during the bite scan process, the quality and accuracy of the bite scan registration may be improved.

Note that though method 200 is described with the left side of the patient's jaw first being scanned followed by the right side of the patient's jaw, it may be equally performed by first scanning the right side of the patient's jaw followed by the left side of the patient's jaw.

Figure 2B:
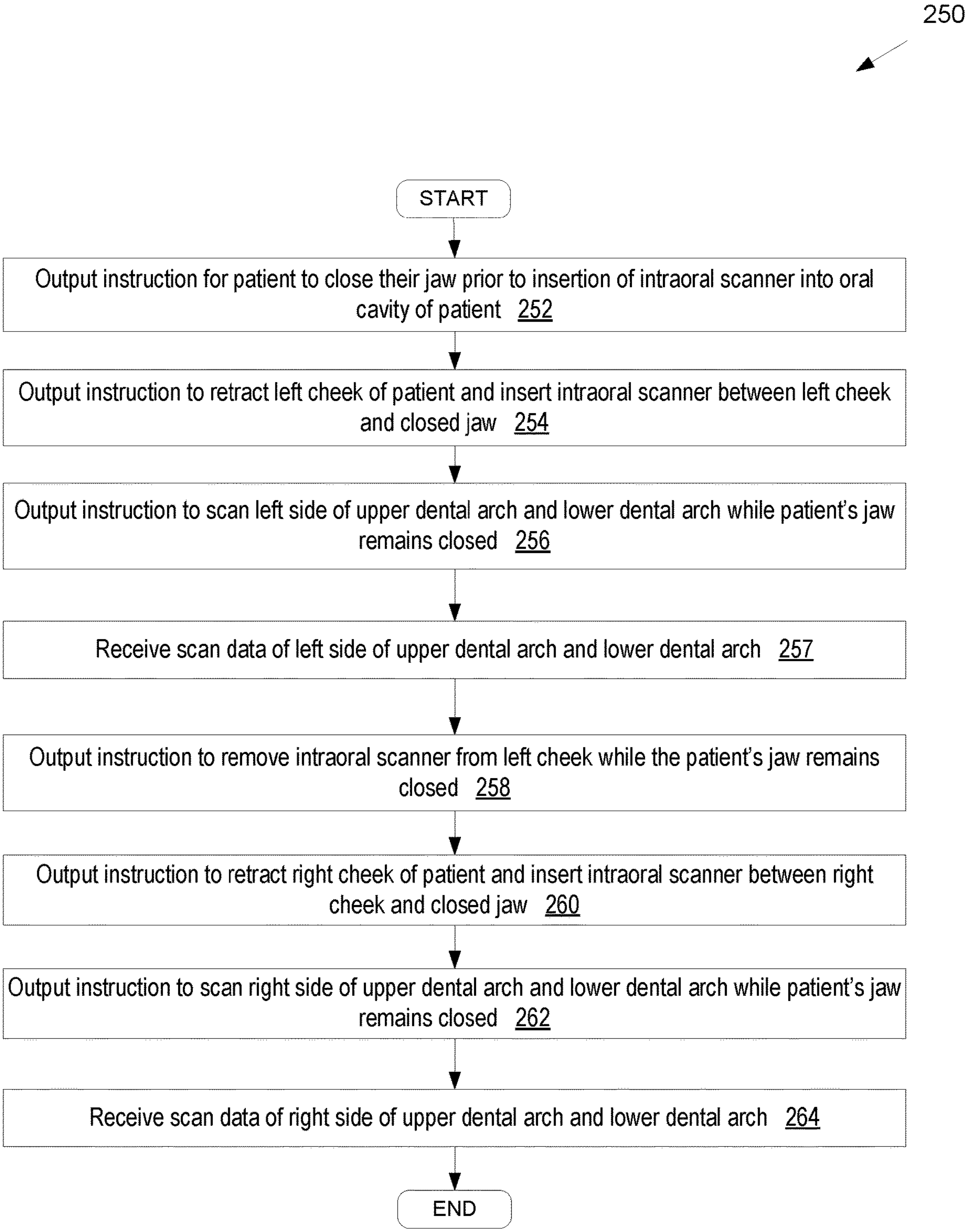
FIG. 2B is a flow chart illustrating an embodiment for a method of guiding a user (e.g., a dental practitioner) to scan a patient bite using an intraoral scanner according to a bite scan protocol.

FIG. 2B is a flow chart illustrating an embodiment for a method 250 of guiding a user (e.g., a dental practitioner) to scan a patient bite using an intraoral scanner according to a bite scan protocol. In embodiments, method 250 may be performed in conjunction with method 200. For example, method 250 may be performed to provide a user of an intraoral scanner with a sequence of instructions that the user may follow to implement a bite scan protocol. In following the instructions of method 250 a user may perform one or more operations of method 200 in some embodiments.

In one embodiment, at block 252 a computing device outputs instructions for a patient to close their jaw prior to insertion of the intraoral scanner into the oral cavity of the patient. In one embodiment, the patient is directed to swallow and to close their jaw after swallowing. This may cause the patient's lower jaw to achieve a natural closed position relative to the upper jaw. Alternatively, the patient may be directed to place their tongue against the top of their palette while they close their mouth, which can also achieve a natural closed position of the lower jaw.

In one embodiment, at block 254 the computing device outputs instructions for a practitioner to retract a first side of the patient's cheeks (e.g., the patient's left cheek) and inserts the intraoral scanner (e.g., the probe of the intraoral scanner) between the first side of the patient's cheeks (e.g., the left cheek) and the closed jaw of the patient. In one embodiment, the cheek is retracted using a specialized cheek retractor tool. The cheek retractor tool may retract the cheek in a manner that does not interfere with a scan or a tip of an intraoral scanner, and that does not impose a force that would cause the patient's jaw to move. Accordingly, the cheek retractor tool is not a part of a scanned area in embodiments. In one embodiment, the intraoral scanner is inserted into the patient's oral cavity while the patient's jaw is still opened, and the patient closes their jaw while the intraoral scanner is inserted between the first side of the patient's cheeks (e.g., left cheek) and the patient's jaw. In one embodiment, this process is performed while the patient swallows or immediately after the patient swallows.

At block 256, the computing device outputs instructions for the practitioner to scan a first side of the upper and lower dental arch (e.g., the left side of the patient's jaw) while the patient's jaw remains closed. This may produce a first set of intraoral scans and/or images that are usable to determine a relative position and/or orientation of the lower dental arch (e.g., the 3D model of the lower dental arch) to the upper dental arch (e.g., the 3D model of the upper dental arch). For accuracy, the other side of the patient's jaw may also be scanned to determine the relative position and/or orientation of the lower dental arch to the upper dental arch.

At block 257, the computing device may receive intraoral scan data of a left side of the upper dental arch and lower dental arch of the patient (e.g., as the scan data is generated).

At block 258, the computing device may output instructions for the practitioner to remove the intraoral scanner from first side of the cheeks (e.g., the left cheek) while the patient's jaw remains closed.

In one embodiment, at block 260 the computing device outputs instructions for the practitioner to retract the second side of the patient's cheeks (e.g., the patient's right cheek) and inserts the intraoral scanner (e.g., the probe of the intraoral scanner) between the first side of the patient's cheeks (e.g., the right cheek) and the closed jaw of the patient. The patient's jaw may remain closed and in the same relative position during scanning of the left and right sides of the jaw.

At block 262, the computing device outputs instructions for the practitioner to scan the second side of the upper and lower dental arch (e.g., the right side of the patient's jaw) while the patient's jaw remains closed. This may produce a second set of intraoral scans and/or images that are usable to determine a relative position and/or orientation of the lower dental arch (e.g., the 3D model of the lower dental arch) to the upper dental arch (e.g., the 3D model of the upper dental arch). After scanning of the second side (e.g., the right side) of the patient's jaw, the intraoral scanner may be removed from the patient's oral cavity, and the patient may open their jaw. In some embodiments, the right side of the patient bite is scanned before the left side of the patient bite. In other embodiments, the left side of the patient bite is scanned before the right side of the patient bite.

At block 264, the computing device may receive intraoral scan data of a right side of the upper dental arch and lower dental arch of the patient (e.g., as the scan data is generated). Note that the order of scanning of the left and right side may be switched without otherwise affecting the bite scan protocol in embodiments. It should also be noted that one or more of the instructions may be provided together in a single operation in some embodiments. For example, the instructions of operations 252, 254 and/or 256 may be output together, the instructions of operations 258, 260 and/or 262 may be output together, and so on.

Figure 3A:
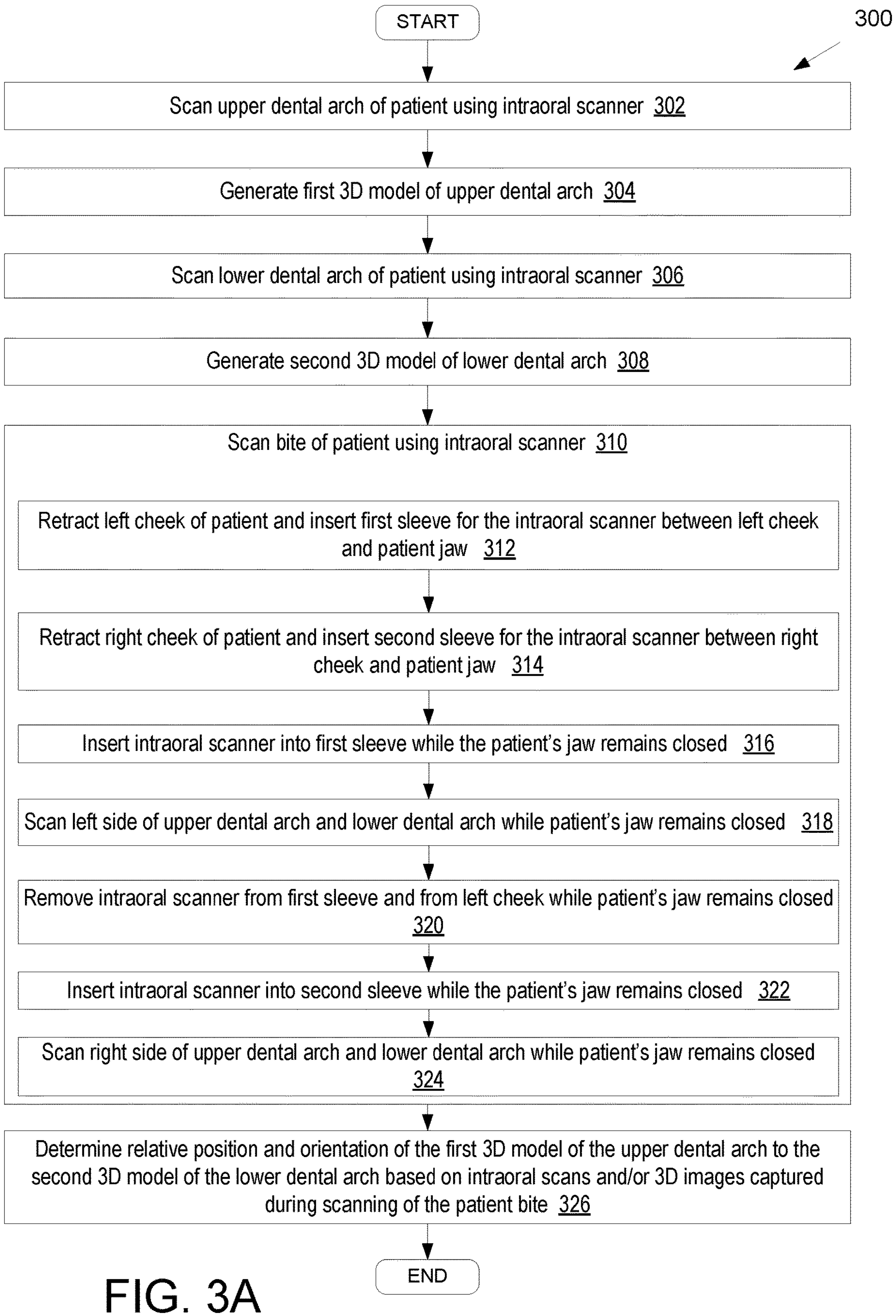
FIG. 3A is a flow chart illustrating an embodiment for a method of scanning a patient bite using an intraoral scanner.

FIG. 3A is a flow chart illustrating an embodiment for a method 300 of scanning a patient bite using an intraoral scanner. At block 302 of method 300, a practitioner (e.g., a doctor, dentist, dental technician, etc.) scans an upper dental arch of a patient using an intraoral scanner to generate a first set of intraoral scan data of the upper dental arch. At block 304, processing logic may generate a first 3D model of the upper dental arch using the first set of intraoral scan data generated from scanning of the upper dental arch. At block 306, the practitioner scans a lower dental arch of the patient using the intraoral scanner to generate a second set of intraoral scan data of the lower dental arch. At block 308, processing logic may generate a second 3D model of the lower dental arch using the second set of intraoral scan data generated from scanning of the lower dental arch. Note that the upper and lower dental arch may be scanned in any order. In some embodiment, the practitioner provides an indication that they are scanning the upper dental arch prior to or after scanning the upper dental arch, and similarly provides an indication that they are scanning the lower dental arch prior to or after scanning the lower dental arch. This may enable the system to identify the scans to use in generating the 3D model of the upper dental arch and the scans to use in generating the 3D model of the lower dental arch.

At block 310, the practitioner scans a bite of the patient using the intraoral scanner. The bite of the patient may be scanned according to a particular bite scan protocol that improves an overall quality of a bite registration and of occlusal contact information in embodiments.

In one embodiment, at block 312 the practitioner retracts the left cheek of the patient and inserts a first sleeve for the intraoral scanner between the left cheek and the patient's jaw. At block 314 the practitioner retracts the right cheek of the patient and inserts a second sleeve for the intraoral scanner between the right cheek and the patient's jaw. The intraoral scanner may fit into the first and second sleeves by sliding the intraoral scanner into the sleeves. The sleeves may have a same general shape and size as a probe of the intraoral scanner, and an opening of the sleeves may protrude from the patient's mouth, one on either side. The sleeves may be inserted while the patient's jaw is closed, or may be inserted while the patient's jaw is opened (in which case the patient would close their jaw after insertion of the first and second sleeves). Whether the sleeves are inserted before or after the patient closes their jaw, the patient may be directed to swallow immediately before or during closing of their jaw. This may cause the patient's lower jaw to achieve a natural closed position relative to the upper jaw.

At block 316, the probe of the intraoral scanner is inserted into the first sleeve while the patient's jaw remains closed. At block 318, the practitioner scans the left side of the upper and lower dental arch (e.g., the left side of the patient's jaw) while the patient's jaw remains closed. This may produce a first set of intraoral scans and/or images that are usable to determine a relative position and/or orientation of the lower dental arch (e.g., the 3D model of the lower dental arch) to the upper dental arch (e.g., the 3D model of the upper dental arch).

At block 320, the practitioner removes the intraoral scanner from the first sleeve and from the left cheek while the patient's jaw remains closed. In one embodiment, the first sleeve remains attached to the intraoral scanner while the scanner is removed from the patient's mouth. After removal of the scanner and sleeve from the patient's mouth, the scanner may be removed from the sleeve. Alternatively, the first sleeve may remain in the patient's mouth when the scanner is removed from the first sleeve and the patient's mouth.

At block 322, the probe of the intraoral scanner is inserted into the second sleeve while the patient's jaw remains closed. At block 324, the practitioner scans the right side of the upper and lower dental arch (e.g., the right side of the patient's jaw) while the patient's jaw remains closed. This may produce a second set of intraoral scans and/or images that are usable to determine a relative position and/or orientation of the lower dental arch (e.g., the 3D model of the lower dental arch) to the upper dental arch (e.g., the 3D model of the upper dental arch). After scanning of the right side of the patient's jaw, the intraoral scanner may be removed from the patient's oral cavity and from the second sleeve, and the patient may open their jaw.

At block 326, processing logic determines a relative position and orientation of the upper dental arch to the lower dental arch and/or movement of the lower dental arch based on the intraoral scans and/or 2D images captured during scanning of the patient bite (e.g., based on the first set of intraoral scans and the second set of intraoral scans). The relative position and orientation of the upper dental arch and lower dental arch may be determined by registering a first region of the intraoral scans (e.g., a region depicting the upper dental arch) to the first 3D model of the upper dental arch and by registering a second region of the intraoral scans (e.g., a region depicting the lower dental arch) to the second 3D model of the lower dental arch. Due to the patient keeping their jaw closed and immobile during the bite scan process, the quality and accuracy of the bite scan registration may be improved.

Note that though method 300 is described with the left side of the patient's jaw first being scanned followed by the right side of the patient's jaw, it may be equally performed by first scanning the right side of the patient's jaw followed by the left side of the patient's jaw.

Figure 3B:
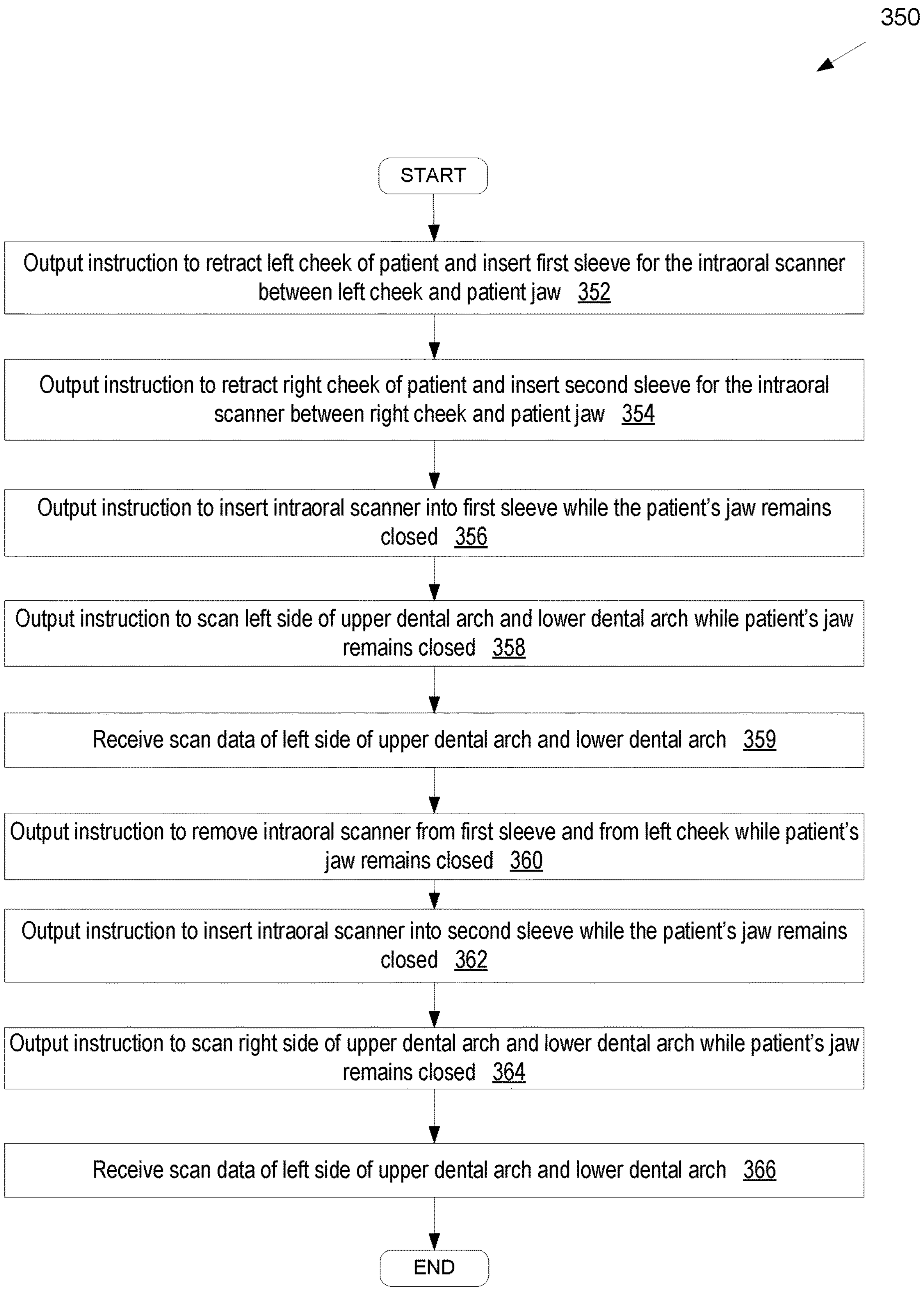
FIG. 3B is a flow chart illustrating an embodiment for a method of guiding a user (e.g., a dental practitioner) to scan a patient bite using an intraoral scanner according to a bite scan protocol.

FIG. 3B is a flow chart illustrating an embodiment for a method 350 of guiding a user (e.g., a dental practitioner) to scan a patient bite using an intraoral scanner according to a bite scan protocol. In embodiments, method 350 may be performed in conjunction with method 300. For example, method 350 may be performed to provide a user of an intraoral scanner with a sequence of instructions that the user may follow to implement a bite scan protocol. In following the instructions of method 350 a user may perform one or more operations of method 300 in some embodiments.

In one embodiment, at block 352 the computing device outputs instructions for a practitioner to retract the left cheek of the patient and insert a first sleeve for the intraoral scanner between the left cheek and the patient's jaw.

At block 354, the computing device outputs instructions for the practitioner to retract the right cheek of the patient and insert a second sleeve for the intraoral scanner between the right cheek and the patient's jaw. The intraoral scanner may fit into the first and second sleeves by sliding the intraoral scanner into the sleeves. The sleeves may have a same general shape and size as a probe of the intraoral scanner, and an opening of the sleeves may protrude from the patient's mouth, one on either side. The sleeves may be inserted while the patient's jaw is closed, or may be inserted while the patient's jaw is opened (in which case the patient would close their jaw after insertion of the first and second sleeves). Whether the sleeves are inserted before or after the patient closes their jaw, the patient may be directed to swallow immediately before or during closing of their jaw. This may cause the patient's lower jaw to achieve a natural closed position relative to the upper jaw.

At block 356, the computing device may output instructions for the probe of the intraoral scanner to be inserted into the first sleeve while the patient's jaw remains closed.

At block 358, the computing device may output instructions for the practitioner to scan the left side of the upper and lower dental arch (e.g., the left side of the patient's jaw) while the patient's jaw remains closed. This may produce a first set of intraoral scans and/or images that are usable to determine a relative position and/or orientation of the lower dental arch (e.g., the 3D model of the lower dental arch) to the upper dental arch (e.g., the 3D model of the upper dental arch).

At block 359, the computing device may receive intraoral scan data of a left side of the upper dental arch and lower dental arch of the patient (e.g., as the scan data is generated).

At block 360, the computing device may output instructions for the practitioner to remove the intraoral scanner from the first sleeve and from the left cheek while the patient's jaw remains closed. In one embodiment, the first sleeve remains attached to the intraoral scanner while the scanner is removed from the patient's mouth. After removal of the scanner and sleeve from the patient's mouth, the scanner may be removed from the sleeve. Alternatively, the first sleeve may remain in the patient's mouth when the scanner is removed from the first sleeve and the patient's mouth.

At block 362, the computing device may output instructions for the probe of the intraoral scanner to be inserted into the second sleeve while the patient's jaw remains closed.

At block 364, the computing device may output instructions for the practitioner to scan the right side of the upper and lower dental arch (e.g., the right side of the patient's jaw) while the patient's jaw remains closed. This may produce a second set of intraoral scans and/or images that are usable to determine a relative position and/or orientation of the lower dental arch (e.g., the 3D model of the lower dental arch) to the upper dental arch (e.g., the 3D model of the upper dental arch). After scanning of the right side of the patient's jaw, the intraoral scanner may be removed from the patient's oral cavity and from the second sleeve, and the patient may open their jaw.

At block 366, the computing device may receive intraoral scan data of a right side of the upper dental arch and lower dental arch of the patient (e.g., as the scan data is generated). Note that the order of scanning of the left and right side may be switched without otherwise affecting the bite scan protocol in embodiments. It should also be noted that one or more of the instructions may be provided together in a single operation in some embodiments. For example, the instructions of operations 352, 354, 356 and/or 358 may be output together, the instructions of operations 360, 362 and/or 364 may be output together, and so on.

Figure 4:
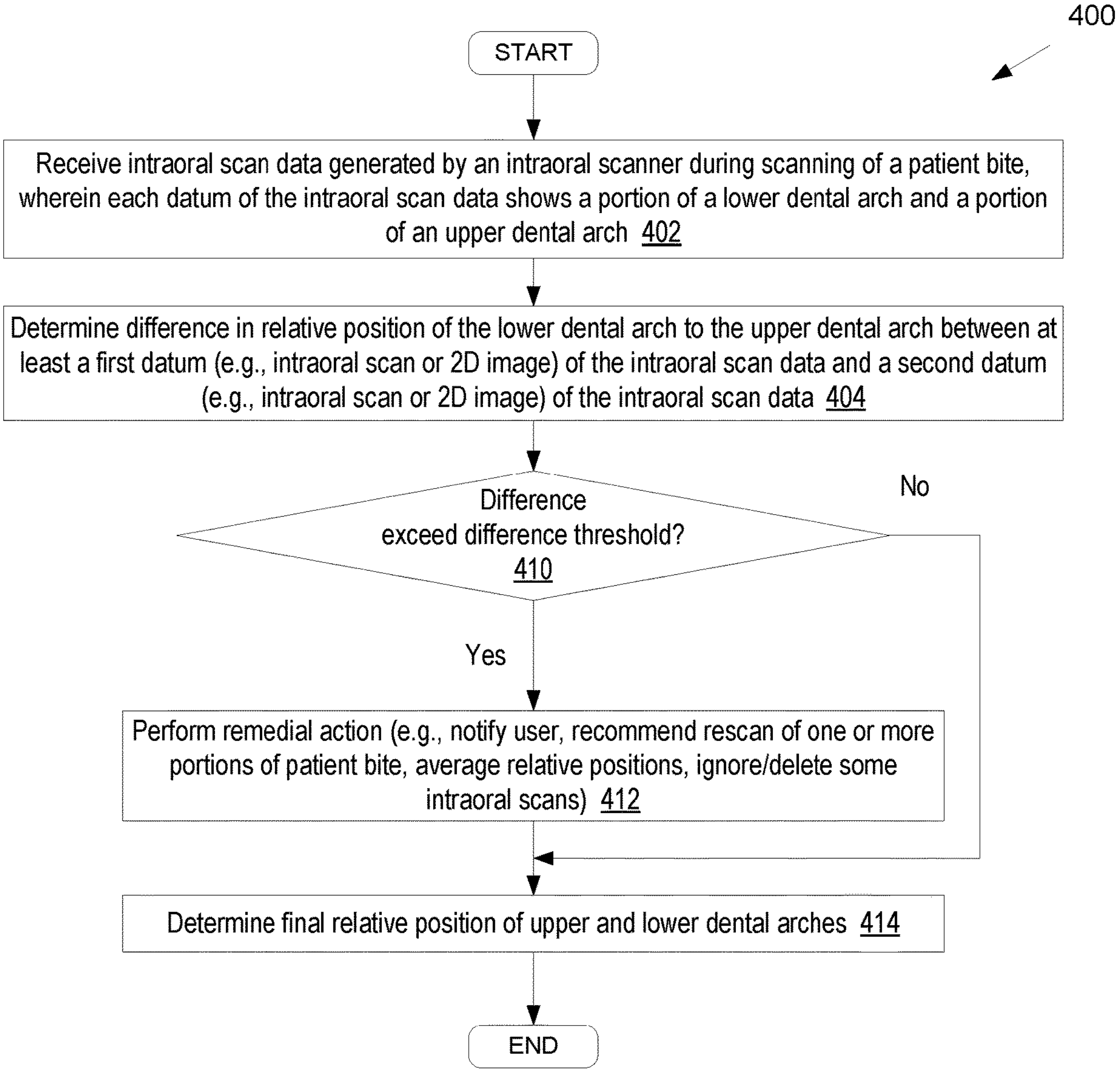
FIG. 4 is a flow chart illustrating an embodiment for a method of determining whether a lower dental arch has moved relative to an upper dental arch during scanning of a patient bite.

FIG. 4 is a flow chart illustrating an embodiment for a method 400 of determining whether a lower dental arch has moved relative to an upper dental arch during scanning of a patient bite. Method 400 may be performed during and/or after scanning of a patient bite. In one embodiment, method 400 is performed during and/or after performance of method 200. In one embodiment, method 400 is performed during and/or after performance of method 300.

At block 402 of method 400, processing logic receives intraoral scan data generated by an intraoral scanner during scanning of a patient bite. In embodiments, the intraoral scan data comprises one or more intraoral scans and/or one or more 2D images (e.g., color images, NIRI images, etc.). In one embodiment, each datum (e.g., each intraoral scan and/or image) of the intraoral scan data shows a portion of a lower dental arch and a portion of an upper dental arch. In some embodiments, one or more of the data may show just a portion of the upper dental arch, just a portion of the lower dental arch, or neither the upper dental arch or the lower dental arch. For example, if intraoral scanning is begun before the intraoral scanner is inserted into the patient's mouth, then some of the intraoral scans and/or images may not show the upper and/or lower dental arches.

In one embodiment, processing logic processes the intraoral scan data (e.g., one or more received images and/or intraoral scans) to determine whether teeth on an upper dental arch and lower dental arch are detected and whether the intraoral scanner is inserted into a patient mouth. Processing logic may also determine whether the patient's jaw is closed. Such determinations may be made, for example, by inputting the intraoral scans and/or images into a trained machine learning model that may output one or more classifications, which may include a first classification that indicates that the scanner is inserted into a patient mouth and upper and lower dental arches are detected, a fourth classification that indicates that the scanner is not inserted into the patient mouth and/or that an upper dental arch and/or lower dental arch are not detected, a third classification that indicates that the patient's jaw is open, a forth classification that indicates that the patient's jaw is closed, and so on. If teeth from an upper dental arch and lower dental arch are detected, and/or the scanner is determined to be in a patient mouth, and/or the patient's jaw is determined to be closed, the method may proceed to block 404. Otherwise, processing logic may output a warning.

At block 404, processing logic determines a difference in bite registration between a first datum (e.g., first intraoral scan or 2D image) and a second datum (e.g., second intraoral scan or 2D image). In one embodiment, the difference in relative position of the lower dental arch to the upper dental arch between the first and second datum is determined by registering and/or comparing the second datum to the first datum and determining a movement of the lower dental arch relative to the upper dental arch based on the registering and/or comparing. For example, two images and/or intraoral scans that were generated close together in time (e.g., that were generated sequentially) may be processed using standard image processing techniques that detect motion. For example, an optical flow may be determined between two images or intraoral scans. The magnitude of the flow vectors in the optical flow may indicate an amount of motion of the lower dental arch between the intraoral scans or images.

If the data being compared was not generated close in time together, or does not have overlapping contents that can be compared (e.g., if one image shows a left side of the patient bite and another image shows a right side of the patient bite, in which case there is no overlapping data between the images), then determination of motion of the lower jaw between the data can be more challenging.

In one embodiment, to determine if a lower jaw has moved relative to an upper jaw (e.g., to determine a difference in relative position of the lower dental arch to the upper dental arch between the first datum of the intraoral scan data and the second datum of the intraoral scan data), a sequence of registration operations is performed. In one embodiment, the difference is determined by a) registering the first datum with a first 3D model of an upper dental arch of the patient and with a second 3D model of the lower dental arch of the patient, b) determining first coordinates of the first 3D model of the upper dental arch and second coordinates of the second 3D model of the lower dental arch for the first datum, and determining the relative positions of the first and second 3D models based on the respective coordinates, c) determining third coordinates of the first 3D model of the upper dental arch and fourth coordinates of the second 3D model of the lower dental arch for the second datum, and determining the relative positions of the first and second 3D models based on the respective coordinates, and d) determining differences in the relative position of the lower dental arch to the upper dental arch based on a comparison of the first, second, third and/or fourth coordinates.

In embodiments, more than two images and/or intraoral scans are compared and/or differences in relative position between the lower dental arch and the upper dental arch between more than two images and/or intraoral scans are determined. In one embodiment, a moving window of intraoral scans and/or images is applied. The moving window may include a certain number of scans and/or images. A first instance of the moving window (e.g., containing images 1-5) may be used to determine a first relative position of the upper and lower dental arches, a second instance of the moving window (e.g., containing images 2-6) may be used to determine a second relative position of the upper and lower dental arches, and the relative positions associated with the various instances of the moving window may be compared to one another to determine if there has been motion of the lower dental arch during the bite scanning.

In some embodiments, a camera (e.g., a 2D camera or 3D camera) is directed towards a patient's face, and generates 2D or 3D images of the patient's face during scanning of the patient bite. The images generated by the camera may show the intraoral scanner in the patient's mouth, a portion of the upper dental arch, a portion of the lower dental arch, and so on. The images generated by the camera may be processed to determine whether there is any motion of the lower dental arch relative to the upper dental arch during the bite scanning. In one embodiment, the images are compared using the above described image processing techniques (e.g., comparing images to generate an optical flow, and determining an amount of movement of the lower dental arch based on the size of flow vectors associated with the lower dental arch in the optical flow).

In some embodiments, multiple images and/or intraoral scans are input into a trained machine learning model, and the trained machine learning model outputs an indication of an amount of movement of the lower dental arch relative to the upper dental arch between the input images and/or scans. In one embodiment, the machine learning model is a trained neural network, such as a convolutional neural network (CNN), a recurrent neural network (RNN), and so on. Examples of trained machine learning models, how to train them, and possible outputs of trained machine learning models are described in U.S. application Ser. No. 17/230,825.

In embodiments, multiple techniques are applied to determine if the lower dental arch has moved relative to the upper dental arch during a patient bite scan. In one embodiment, a first technique (e.g., that uses direct comparison of images and/or scans to one another) is used to determine relative motion of the lower jaw to the upper jaw for continuously or sequentially generated frames (e.g., scans and/or images). In one embodiment, a second technique (e.g., that relies on registration to 3D models) is used to determine relative motion of the lower jaw to the upper jaw for images and/or scans that cannot be compared to one another (e.g., where there are no overlapping or shared image contents that can be compared).

In some embodiments, one or more moving tissue and/or excess material detection techniques are applied to identify moving tissue and/or excess material such as cheeks, tongue, etc., and detected moving tissue and/or excess material is filtered out of or removed from images and/or intraoral scans prior to determination of jaw movement and/or relative positions of upper and lower dental arches. Example moving tissue and/or excess material detection and removal techniques are set forth in U.S. Application No. 63/326,807, filed Apr. 1, 2022, entitled “System and Method of Scanning Teeth for Restorative Dentistry”, in U.S. application Ser. No. 16/837,960, filed Apr. 1, 2020, entitled “Method and Apparatus for Excessive Materials Removal from Intraoral Scans”, and in U.S. application Ser. No. 16/865,162, filed May 1, 2020, entitled “Excess Material Removal Using Machine Learning”, each of which is incorporated by reference herein in its entirety.

At block 410, processing logic may compare the determined difference in relative position of the lower dental arch to the upper dental arch to a difference threshold. If the determined difference exceeds the difference threshold, the method may proceed to block 412. Otherwise, the method may proceed to block 414.

At block 412, processing logic may perform one or more remedial action. Examples of remedial actions include notifying a user that the difference threshold has been exceeded and/or that the lower jaw has moved an unacceptable amount during the bite scan, recommending a rescan of one or more portions of the patient bite (e.g., of the upper and lower dental arches while the patient's jaw is closed), averaging the determined relative positions of the upper and lower dental arches, ignoring or deleting one or more intraoral scans, and so on. In one embodiment, a user may be directed to rescan one side of the patient's bite, or a specific region where an unacceptable uncertainty is determined.

The operations of blocks 402-412 may be repeated in a loop as additional intraoral scans and/or images are received. As each new intraoral scan and/or image is received, one or more of the above described analysis techniques may be performed to determine if the lower jaw has moved relative to the upper jaw during the scanning of the patient bite. These operations may be performed in parallel with operations of a bite registration process. If at any point during the bite scanning a determination is made that the patients jaw has moved too much, then remedial actions may be implemented while the bite scanning is still ongoing.

At block 414, processing logic determines a final relative position of the upper and lower dental arches. The final relative position may be determined based on performing a bite registration process. In one embodiment, the bite registration process may include, for each intraoral scan and/or image generated during intraoral scanning of the patient bite, registering the upper dental arch to a first region of the intraoral scan or image that shows a portion of the upper dental arch, registering the lower dental arch to a second region of the intraoral scan or image that shows a portion of the lower dental arch, and determining a relative position and/or orientation of the second 3D model to the first 3D model based on the respective registrations. The bite registration process may further include comparing and/or averaging the respective relative positions and/or orientations of the lower dental arch to the upper dental arch determined for each of the intraoral scans and/or images.

In one embodiment, the bite registration process may include registering each of the intraoral scans generated of a left side of the patient bite together to generate a 3D surface, and then registering the 3D surface to the first 3D model of the upper dental arch and the second 3D model of the lower dental arch. The bite registration process may further include registering each of the intraoral scans of the right side of the patient bite together to generate another 3D surface, and then registering the other 3D surface to the first 3D model of the upper dental arch and the second 3D model of the lower dental arch. A first relative position of the upper and lower dental arches may be determined for the left side of the patient bite and a second relative position of the upper and lower dental arches may be determined for the right side of the patient bite. These relative positions of the upper and lower dental arches may then be averaged together to generate the final relative position of the upper and lower dental arches.

Figure 5:
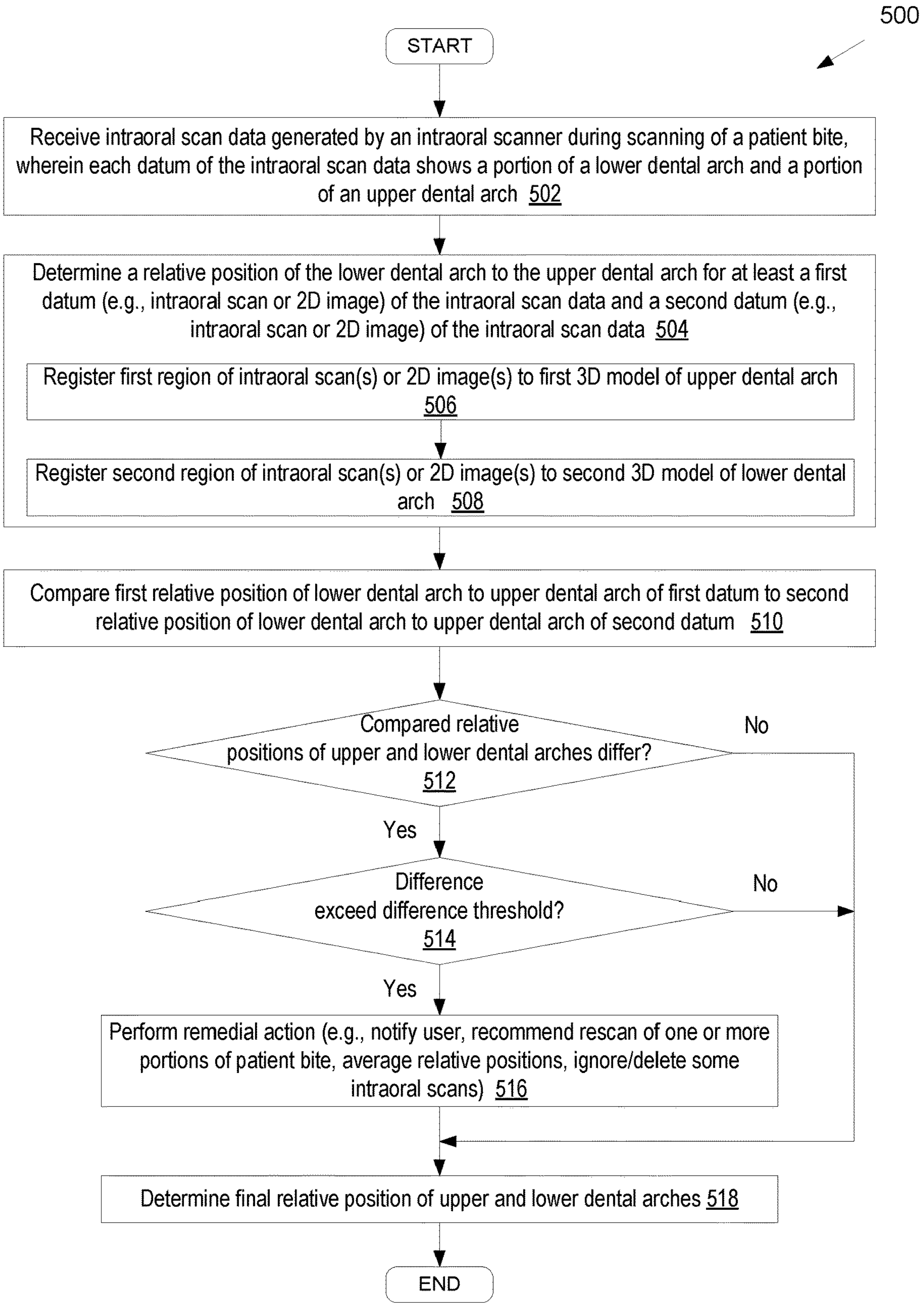
FIG. 5 is a flow chart illustrating an embodiment for a method of determining whether a lower dental arch has moved relative to an upper dental arch during scanning of a patient bite.

FIG. 5 is a flow chart illustrating an embodiment for a method 500 of determining whether a lower dental arch has moved relative to an upper dental arch during scanning of a patient bite. Method 500 may be performed during and/or after scanning of a patient bite. In one embodiment, method 500 is performed during and/or after performance of method 200. In one embodiment, method 500 is performed during and/or after performance of method 300.

At block 502 of method 500, processing logic receives intraoral scan data generated by an intraoral scanner during scanning of a patient bite. In embodiments, the intraoral scan data comprises one or more intraoral scans and/or one or more 2D images (e.g., color images, NIRI images, etc.). In one embodiment, each datum (e.g., each intraoral scan and/or image) of the intraoral scan data shows a portion of a lower dental arch and a portion of an upper dental arch. In some embodiments, one or more of the data may show just a portion of the upper dental arch, just a portion of the lower dental arch, or neither the upper dental arch or the lower dental arch. For example, if intraoral scanning is begun before the intraoral scanner is inserted into the patient's mouth, then some of the intraoral scans and/or images may not show the upper and/or lower dental arches.

At block 504, processing logic determines a relative position of the lower dental arch to the upper dental arch for at least a first datum (e.g., a first intraoral scan or 2D image) of the intraoral scan data and a second datum (e.g., a second intraoral scan or 2D image) of the intraoral scan data. In one embodiment, the first datum is a first 3D surface generated by registering together a sequence of intraoral scans (e.g., that were generated of a first side of the patient's mouth). In one embodiment, the second datum is a second 3D surface generated by registering together another sequence of intraoral scans (e.g., that were generated of a second side of the patient's mouth). In one embodiment, determining the relative position of the lower dental arch to the upper dental arch for a datum includes performing the operations of block 506 and 508 for the datum. At block 506, processing logic registers a first region of a datum (e.g., of an intraoral scan, 2D image, or a 3D surface) to a first 3D model of the upper dental arch. At block 508, processing logic registers a second region of the datum to a second 3D model of the lower dental arch. The relative position of the lower dental arch to the upper dental arch may then be determined since the first and second 3D model have been registered to the same reference frame.

At block 510, processing logic compares the first relative position of the lower dental arch to the upper dental arch of the first datum to the second relative position of the lower dental arch to the upper dental arch of the second datum. At block 512, processing logic determines a difference in the relative positions of the lower dental arch to the upper dental arch (e.g., whether the lower dental arch have moved relative to the upper dental arch) based on the comparison. If there is no detectable difference, then the method may proceed to block 518. If a difference is detected, the method may continue to block 514.

At block 514, processing logic determines whether the detected difference exceeds a difference threshold. If the difference is below the difference threshold, then the method proceeds to block 518. If the difference meets or exceeds the difference threshold, the method continues to block 516.

At block 516, processing logic may perform one or more remedial action. Examples of remedial actions include notifying a user that the difference threshold has been exceeded and/or that the lower jaw has moved an unacceptable amount during the bite scan, recommending a rescan of one or more portions of the patient bite (e.g., of the upper and lower dental arches while the patient's jaw is closed), averaging the determined relative positions of the upper and lower dental arches, ignoring or deleting one or more intraoral scans, and so on.

The operations of blocks 502-516 may be repeated in a loop as additional intraoral scans and/or images are received. These operations may be performed in parallel with operations of a bite registration process. If at any point during the bite scanning a determination is made that the patients jaw has moved too much, then remedial actions may be implemented while the bite scanning is still ongoing.

At block 518, processing logic determines a final relative position of the upper and lower dental arches. The final relative position may be determined based on performing a bite registration process.

Figure 6:
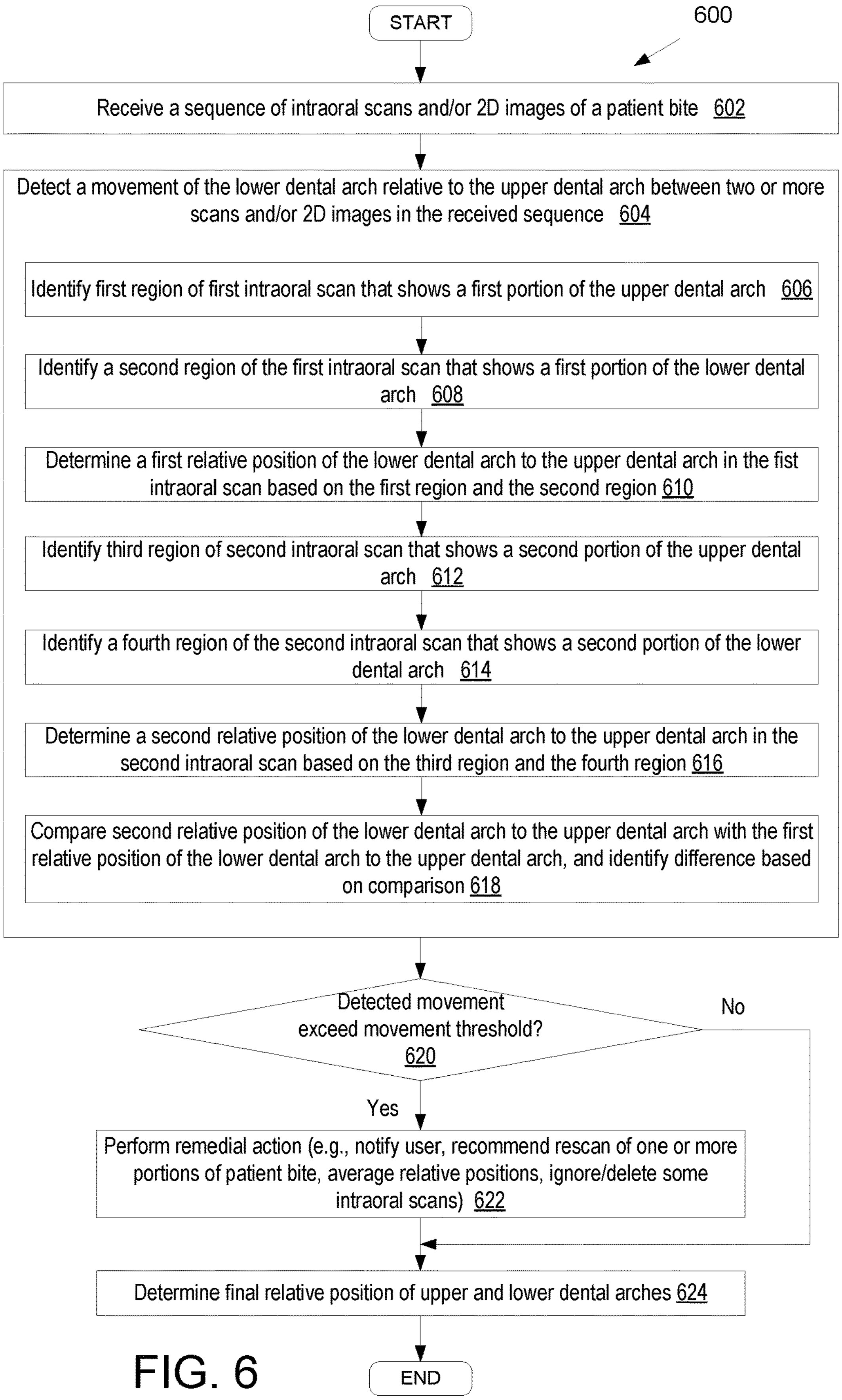
FIG. 6 is a flow chart illustrating an embodiment for a method of determining whether a lower dental arch has moved relative to an upper dental arch during scanning of a patient bite.

FIG. 6 is a flow chart illustrating an embodiment for a method 600 of determining whether a lower dental arch has moved relative to an upper dental arch during scanning of a patient bite. Method 600 may be performed during and/or after scanning of a patient bite. In one embodiment, method 600 is performed during and/or after performance of method 200. In one embodiment, method 600 is performed during and/or after performance of method 300.

At block 602 of method 600, processing logic receives intraoral scan data generated by an intraoral scanner during scanning of a patient bite. In embodiments, the intraoral scan data comprises a sequence of intraoral scans and/or 2D images (e.g., color images, NIRI images, etc.) of the patient bite.

At block 604, processing logic detects a movement of the lower dental arch relative to the upper dental arch between two or more intraoral scans and/or 2D images in the received sequence. In one embodiment, processing logic performs processing on intraoral scans in the sequence to detect movement between the intraoral scans (e.g., by determining a 3D optical flow between intraoral scans). In one embodiment, processing logic performs image processing on images in the sequence to detect movement between the images (e.g., by determining an optical flow between images). This may be performed, for example, for images that have significant overlapping contents. In one embodiment, processing logic performs registration of images and/or intraoral scans to 3D models to determine relative positions of lower dental arches to upper dental arches. Such a techniques may be performed whether or not there is overlapping content between the images and/or intraoral scans.

In one embodiment, at block 606, processing logic identifies a first region of a first intraoral scan that shows a first portion of the upper dental arch. At block 608, processing logic identifies a second region of the first intraoral scan that shows a first portion of the lower dental arch. At block 610, processing logic determines a first relative position of the lower dental arch to the upper dental arch in the first intraoral scan based on the first region and the second region. For example, processing logic may determine an outline of teeth on the upper dental arch in the first region and an outline of teeth on the lower dental arch in the second region, and may measure a first distance between an edge of a tooth on the upper dental arch and an edge of a tooth on the lower dental arch.

At block 612, processing logic identifies a third region of a second intraoral scan that shows a second portion of the upper dental arch. At block 614, processing logic identifies a fourth region of the second intraoral scan that shows a second portion of the lower dental arch. At block 616, processing logic determines a second relative position of the lower dental arch to the upper dental arch in the second intraoral scan based on the third region and the fourth region. For example, processing logic may determine an outline of teeth on the upper dental arch in the third region and an outline of teeth on the lower dental arch in the fourth region, and may measure a second distance between an edge of a tooth on the upper dental arch and an edge of a tooth on the lower dental arch.

At block 618, processing logic may compare the second relative position of the lower dental arch to the upper dental arch (e.g., the second distance between teeth on the upper and lower dental arch) to the first relative position of the lower dental arch to the upper dental arch (e.g., the first distance between teeth on the upper dental arch and the lower dental arch). Based on such a comparison, processing logic may determine a difference in the relative positions between the intraoral scans (e.g., by subtracting the second distance from the first distance). The determined difference may reflect an amount of movement of the lower dental arch relative to the upper dental arch during the bite scanning process.

At block 614, processing logic determines whether the detected difference or jaw movement exceeds a movement threshold or difference threshold. If the movement is below the threshold, then the method proceeds to block 624. If the detected amount of movement meets or exceeds the threshold, the method continues to block 622.

At block 622, processing logic may perform one or more remedial action. Examples of remedial actions include notifying a user that the difference threshold has been exceeded and/or that the lower jaw has moved an unacceptable amount during the bite scan, recommending a rescan of one or more portions of the patient bite (e.g., of the upper and lower dental arches while the patient's jaw is closed), averaging the determined relative positions of the upper and lower dental arches, ignoring or deleting one or more intraoral scans, and so on.

The operations of blocks 602-622 may be repeated in a loop as additional intraoral scans and/or images are received. These operations may be performed in parallel with operations of a bite registration process. If at any point during the bite scanning a determination is made that the patients jaw has moved too much, then remedial actions may be implemented while the bite scanning is still ongoing.

At block 624, processing logic determines a final relative position of the upper and lower dental arches. The final relative position may be determined based on performing a bite registration process.

Figure 7:
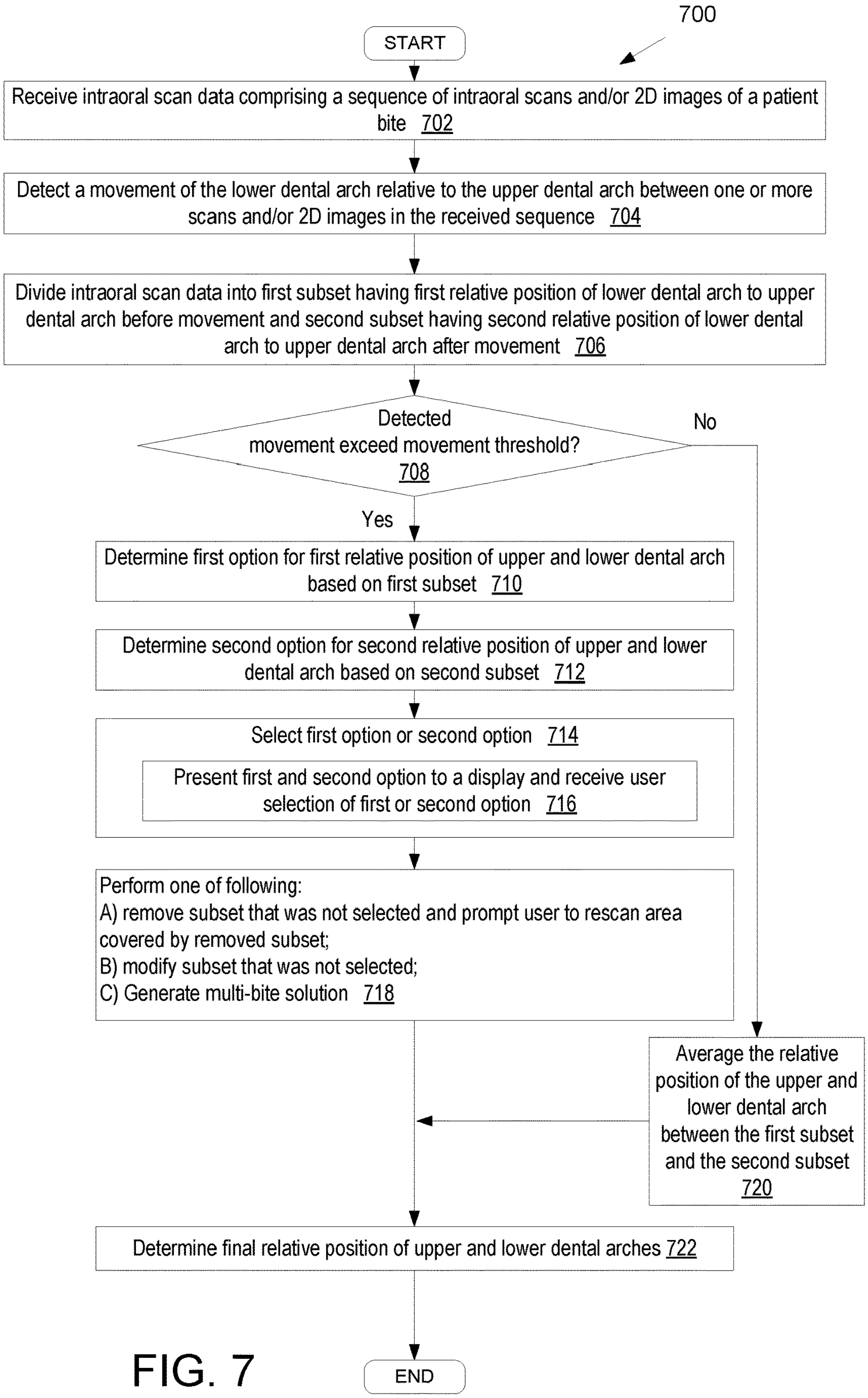
FIG. 7 is a flow chart illustrating an embodiment for a method of determining relative positions of upper and lower dental arches of a patient.

FIG. 7 is a flow chart illustrating an embodiment for a method 700 of determining relative positions of upper and lower dental arches of a patient. Method 700 may be performed during and/or after scanning of a patient bite. In one embodiment, method 700 is performed during and/or after performance of method 200. In one embodiment, method 700 is performed during and/or after performance of method 300.

At block 702 of method 700, processing logic receives intraoral scan data generated by an intraoral scanner during scanning of a patient bite. In embodiments, the intraoral scan data comprises a sequence of intraoral scans and/or 2D images (e.g., color images, NIRI images, etc.). In one embodiment, each datum (e.g., each intraoral scan and/or image) of the intraoral scan data shows a portion of a lower dental arch and a portion of an upper dental arch. In some embodiments, one or more of the data may show just a portion of the upper dental arch, just a portion of the lower dental arch, or neither the upper dental arch or the lower dental arch. For example, if intraoral scanning is begun before the intraoral scanner is inserted into the patient's mouth, then some of the intraoral scans and/or images may not show the upper and/or lower dental arches.

At block 704, processing logic detects movement of the lower dental arch relative to the upper dental arch between one or more scans and/or 2D images in the received sequence. In one embodiment, detecting the movement includes determining a difference in bite registration between a first datum (e.g., first intraoral scan or 2D image) and a second datum (e.g., second intraoral scan or 2D image). In one embodiment, the difference in relative position of the lower dental arch to the upper dental arch between the first and second datum is determined by registering and/or comparing the second datum to the first datum and determining a movement of the lower dental arch relative to the upper dental arch based on the registering and/or comparing. For example, two images and/or intraoral scans that were generated close together in time (e.g., that were generated sequentially) may be processed using standard image processing techniques that detect motion. For example, an optical flow may be determined between two images or intraoral scans. The magnitude of the flow vectors in the optical flow may indicate an amount of motion of the lower dental arch between the intraoral scans or images.

In one embodiment, the difference is determined by a) registering the first datum with a first 3D model of an upper dental arch of the patient and with a second 3D model of the lower dental arch of the patient, b) determining first coordinates of the first 3D model of the upper dental arch and second coordinates of the second 3D model of the lower dental arch for the first datum, and determining the relative positions of the first and second 3D models based on the respective coordinates, c) determining third coordinates of the first 3D model of the upper dental arch and fourth coordinates of the second 3D model of the lower dental arch for the second datum, and determining the relative positions of the first and second 3D models based on the respective coordinates, and d) determining differences in the relative position of the lower dental arch to the upper dental arch based on a comparison of the first, second, third and/or fourth coordinates.

In embodiments, more than two images and/or intraoral scans are compared and/or differences in relative position between the lower dental arch and the upper dental arch between more than two images and/or intraoral scans are determined. In one embodiment, a moving window of intraoral scans and/or images is applied. The moving window include a certain number of scans and/or images. A first instance of the moving window (e.g., containing images 1-5) may be used to determine a first relative position of the upper and lower dental arches, a second instance of the moving window (e.g., containing images 2-6) may be used to determine a second relative position of the upper and lower dental arches, and the relative positions associated with the various instances of the moving window may be compared to one another to determine if there has been motion of the lower dental arch during the bite scanning.

In some embodiments, a camera (e.g., a 2D camera or 3D camera) is directed towards a patient's face, and generates 2D or 3D images of the patient's face during scanning of the patient bite. The images generated by the camera may show the intraoral scanner in the patient's mouth, a portion of the upper dental arch, a portion of the lower dental arch, and so on. The images generated by the camera may be processed to determine whether there is any motion of the lower dental arch relative to the upper dental arch during the bite scanning. In one embodiment, the images are compared using the above described image processing techniques (e.g., comparing images to generate an optical flow, and determining an amount of movement of the lower dental arch based on the size of flow vectors associated with the lower dental arch in the optical flow).

In some embodiments, multiple images and/or intraoral scans are input into a trained machine learning model, and the trained machine learning model outputs an indication of an amount of movement of the lower dental arch relative to the upper dental arch between the input images and/or scans. In one embodiment, the machine learning model is a trained neural network, such as a convolutional neural network (CNN), a recurrent neural network (RNN), and so on.

In embodiments, multiple techniques are applied to determine if the lower dental arch has moved relative to the upper dental arch during a patient bite scan. In one embodiment, a first technique (e.g., that uses direct comparison of images and/or scans to one another) is used to determine relative motion of the lower jaw to the upper jaw for continuously or sequentially generated frames (e.g., scans and/or images). In one embodiment, a second technique (e.g., that relies on registration to 3D models) is used to determine relative motion of the lower jaw to the upper jaw for images and/or scans that cannot be compared to one another (e.g., where there are no overlapping or shared image contents that can be compared).

In some embodiments, processing logic determines one or more point in time at which the lower dental arch moved. Processing logic may determine, for example, that the lower jaw moved between capture of a first intraoral scan or image and a second intraoral scan or image that is a next scan after the first intraoral scan. At block 706, processing logic divides the intraoral scan data into a first subset having a first relative position of the lower dental arch to the upper dental arch before the movement (e.g., including the first intraoral scan or image and intraoral scans and/or images generated before the first intraoral scan or image) and a second subset having a second relative position of the lower dental arch to the upper dental arch after the movement (e.g., including the second intraoral scan or image and intraoral scans and/or images generated after the second intraoral scan or image).

At block 708, processing logic may determine a magnitude of the movement of the lower jaw between the first subset and the second subset. The difference may be determined, for example, by generating a first 3D surface using the first subset, generating a second 3D surface using the second subset, and comparing the first 3D surface to the second 3D surface. In one embodiment, the difference is determined by generating a first 3D surface from the first subset, and registering the first 3D surface to a first 3D model of an upper dental arch and to a second 3D model of a lower dental arch; generating a second 3D surface from the second subset, and registering the second 3D surface to the first 3D model of the upper dental arch and to the second 3D model of the lower dental arch; and comparing the relative position of the first 3D model to the second 3D model determined from registering of the first 3D surface to the first and second 3D models to the relative position of the first 3D model to the second 3D model determined from registering of the second 3D surface to the first and second 3D models. The magnitude of movement may be compared to one or more movement threshold. If the detected movement exceeds the movement threshold, then the method continues to block 710. Otherwise the method proceeds to block 720, at which processing logic may average the relative position of the upper and lower dental arch between the first subset and the second subset.

At block 710, processing logic determines a first option for a first relative position of the upper and lower dental arch based on the first subset (e.g., based on registering the first and second 3D models to the first 3D surface generated from the first subset). At block 712, processing logic determines a second option for a second relative position of the upper and lower dental arch based on the second subset (e.g., based on registering the first and second 3D models to the second 3D surface generated from the second subset).

At block 714, processing logic may select the first option or the second option for the relative position of the upper and lower dental arches. In one embodiment, this includes at block 716 presenting the first and second options to a display and receiving a user selection of the first option or the second option. A practitioner may view the relative positions of the upper and lower dental arch for each of the options side by side, and may zoom in, zoom out, pan in one or more directions, rotate about one or more axes, etc. to view the possible options.

In one embodiment, at block 718 processing logic removes, ignores, or filters out the subset that was not selected. Processing logic may then determine the relative positions of the upper and lower dental arches without the subset that was not selected. If the subset that was not selected includes only a small number of intraoral scans and/or images (e.g., the movement of the jaw occurred shortly after the scanning began or shortly before the scanning ended, resulting in only a small number of initial intraoral scans or final intraoral scans being removed or ignored), then there may still be sufficient intraoral scans to accurately determine the relative positions of the upper and lower dental arches. However, if too many intraoral scans were removed or ignored, then additional scanning of the patient bite may be recommended. Accordingly, processing logic may determine whether the scans from the first subset are sufficient, and if they are not sufficient then processing logic may prompt a user to rescan an area that was covered by the removed subset. For example, if the left side of the patient's bite was in the removed subset, then the practitioner may be prompted to rescan the left side of the patient's bite.

In one embodiment, at block 718 processing logic modifies the subset that was not selected. As discussed above, a first 3D surface may have been generated from the first subset of the intraoral scan data and a second 3D surface may have been generated from the second subset of the intraoral scan data. These 3D surfaces may each have been registered to a first 3D model of an upper dental arch and a second 3D surface of a lower dental arch. Based on such respective registrations, a difference in positioning of the lower dental arch to the upper dental arch may be determined for each of the subsets of intraoral scan data. Such positioning may be used to determine an offset and/or rotation to apply to each datum (e.g., intraoral scan and/or image) from the subset that was not selected to cause the relative position of the lower dental arch to the upper dental arch in that datum to match or approximately match the relative position of the lower dental arch to the upper dental arch from the selected subset.

In one embodiment, at block 718 processing logic generates a multi-bite solution using the first and second subsets. In a multi-bite scenario, different bites may be recorded, which show a different relation between the upper and lower jaw. Processing logic may detect discrepancies between bites as described above, and determine whether such discrepancies merely represent variations of a single bite or whether such discrepancies represent multiple different bites (referred to as multi-bite detection). For example, if the magnitude of the detected jaw movement exceeds an upper movement threshold (which may be above a movement threshold used to determine if the first and second subsets are different enough that they cannot be averaged), processing logic may determine that two different bites are detected, and that a multi-bite scenario has occurred. In some instances, the multiple bites are at the direction of the doctor, who may have instructed a patient to bite in different ways. The system in embodiments can automatically detect, using the application of machine learning or based on comparison of multiple bite scans, such a multi-bite scenario.

In one embodiment, a user is presented with options to perform one of removing the subset that was not selected, modifying the subset that was not selected, or generating the multi-bite solution. Alternatively, processing logic may automatically select which of these options to perform based on an analysis of the first and subsets. In one embodiment, processing logic determines which option to select based on the magnitude of the determined movement of the lower jaw between the first and second subsets.

In an example, a doctor may need to go in and out of the oral cavity with the scanner 150 and wait a few seconds. Scans of bite parts may be recorded separately. Sometimes unintended motion can create discrepancies in the scans of the bites. To understand if this is an intended multi-bite, or an error, the system may output an indication of a potential multi-bite, and ask the doctor for confirmation. Alternatively, the system may automatically make a determination as to whether or not a multi-bite is present. Processing logic may take into consideration the bite locations (e.g., the difference between the different bites) and/or times of taking the scans associated with the bites when making such a determination. This feature may be useful in cases that include bite elevation.

With regards to multi-bite detection, a few possible scenarios include: (a) both sides of the mouth give the same bite relation, indicating that everything is okay and that it is not a multi-bite case; and (b) both sides of the mouth give different bite relation, indicating a need to determine if it is a distortion or a multi-bite case. In embodiments, to decide whether a detected discrepancy is due to distortion or a multi-bite case, the system may take into consideration both time lag between two bite scans and a magnitude of the change or difference in the bite between the two scans. In on embodiment, a time lag (e.g., which may be measured in seconds) between two bite scans is determined, and the time lag is compared to a time lag threshold. The time lag threshold may be, for example, 1 second, 2 seconds, 4 seconds, 10 seconds, and so on. In one embodiment, the two bite scans are compared, and a difference in the bite between the two scans is computed (e.g., which may be measured in microns). The bite difference may then be compared to a bite difference threshold. The bite difference threshold may be, for example, 50 microns, 75 microns, 100 microns, 150 microns, 200 microns, and so on. In one embodiment, if the time lag exceeds the time lag threshold and the bite difference exceeds the bite difference threshold, processing logic determines that the two bite scans represent a multi-bite scenario and generates two different bite solutions.

The operations of blocks 702-720 may be repeated in a loop as additional intraoral scans and/or images are received. As each new intraoral scan and/or image is received, one or more of the above described analysis techniques may be performed to determine if the lower jaw has moved relative to the upper jaw during the scanning of the patient bite. These operations may be performed in parallel with operations of a bite registration process. If at any point during the bite scanning a determination is made that the patients jaw has moved too much, then remedial actions may be implemented while the bite scanning is still ongoing.

At block 722, processing logic determines a final relative position of the upper and lower dental arches. The final relative position may be determined based on performing a bite registration process. In one embodiment, the operations of blocks 704-720 are repeated after scanning is complete. The algorithms applied after scanning is complete may be more processor intensive and take more time to complete, but may be more accurate.

Figure 8:
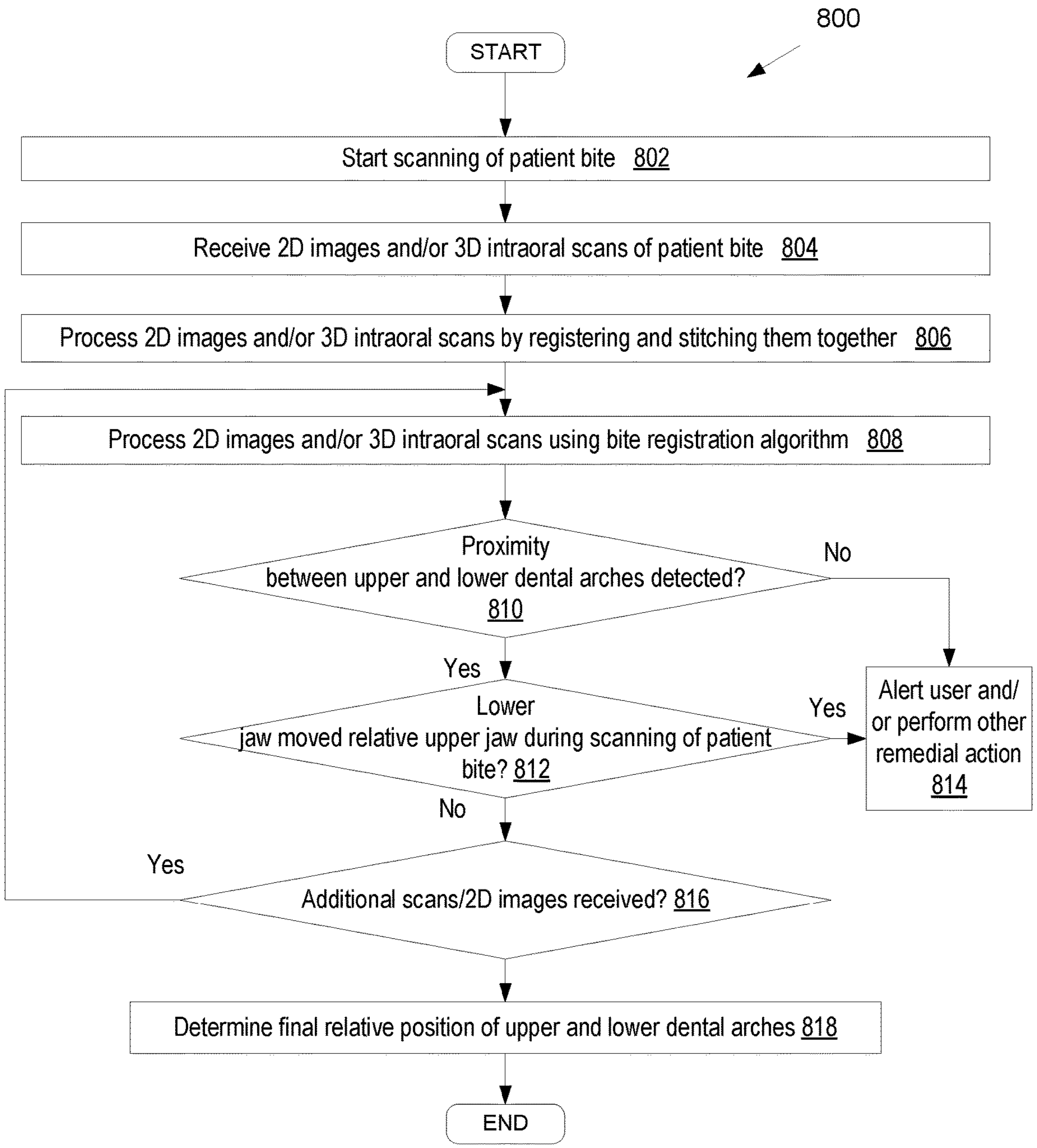
FIG. 8 is a flow chart illustrating an embodiment for a method of determining relative positions of upper and lower dental arches of a patient.

FIG. 8 is a flow chart illustrating an embodiment for a method 800 of determining relative positions of upper and lower dental arches of a patient. Method 800 may be performed during and/or after scanning of a patient bite. In one embodiment, method 800 is performed during and/or after performance of method 200. In one embodiment, method 800 is performed during and/or after performance of method 300.

At block 802 of method 800, scanning of a patient bite begins. At block 804, processing logic receives intraoral scan data generated by an intraoral scanner during scanning of a patient bite. In embodiments, the intraoral scan data comprises one or more intraoral scans and/or one or more 2D images (e.g., color images, NIRI images, etc.). In one embodiment, each datum (e.g., each intraoral scan and/or image) of the intraoral scan data shows a portion of a lower dental arch and a portion of an upper dental arch. In some embodiments, one or more of the data may show just a portion of the upper dental arch, just a portion of the lower dental arch, or neither the upper dental arch or the lower dental arch. For example, if intraoral scanning is begun before the intraoral scanner is inserted into the patient's mouth, then some of the intraoral scans and/or images may not show the upper and/or lower dental arches.

At block 806, processing logic processes the 2D images and/or 3D intraoral scans by registering and stitching them together to generate a 3D surface. At block 808, processing logic processes the 2D images and/or 3D intraoral scans using a bite registration algorithm, which may include registering the 3D surface generated at block 806 to a first 3D model of the patient's upper dental arch and a second 3D model of the patient's lower dental arch. In embodiments, the operations of blocks 806 and 808 may be combined.

In one embodiment, processing logic processes the intraoral scan data (e.g., one or more received images and/or intraoral scans) to determine a proximity between the teeth of the upper and lower dental arches. The detected proximity may be compared to a proximity threshold. If the upper and lower dental arches are not in close proximity (e.g., distance between teeth on upper and lower dental arches is greater than a distance threshold), then the method may proceed to block 814, and a user may be alerted and/or a remedial action may be performed. If the upper and lower dental arches are in close proximity (e.g., distance between teeth on upper and lower dental arch is less than or equal to a distance threshold), the method continues to block 812.

At block 812, processing logic determines whether the lower jaw moved relative to the upper jaw during scanning of the patient bite. Such as determination may be made using any one or more of the techniques described herein above. If the lower jaw is determined to have moved more than a threshold amount relative to the upper dental arch (e.g., more than 0 mm, 10 mm, 20 mm, etc.), then the method proceeds to block 814 and a user is alerted and/or another remedial action is performed. The lower jaw has not moved more than the threshold amount, the method continues to block 816.

At block 816, processing logic determines whether additional intraoral scans and/or images have been received. If so, the method returns to block 808. If scanning of the patient bite is complete, the method proceeds to block 818, and final relative positions of the upper and lower dental arches are determined.

Figure 9:
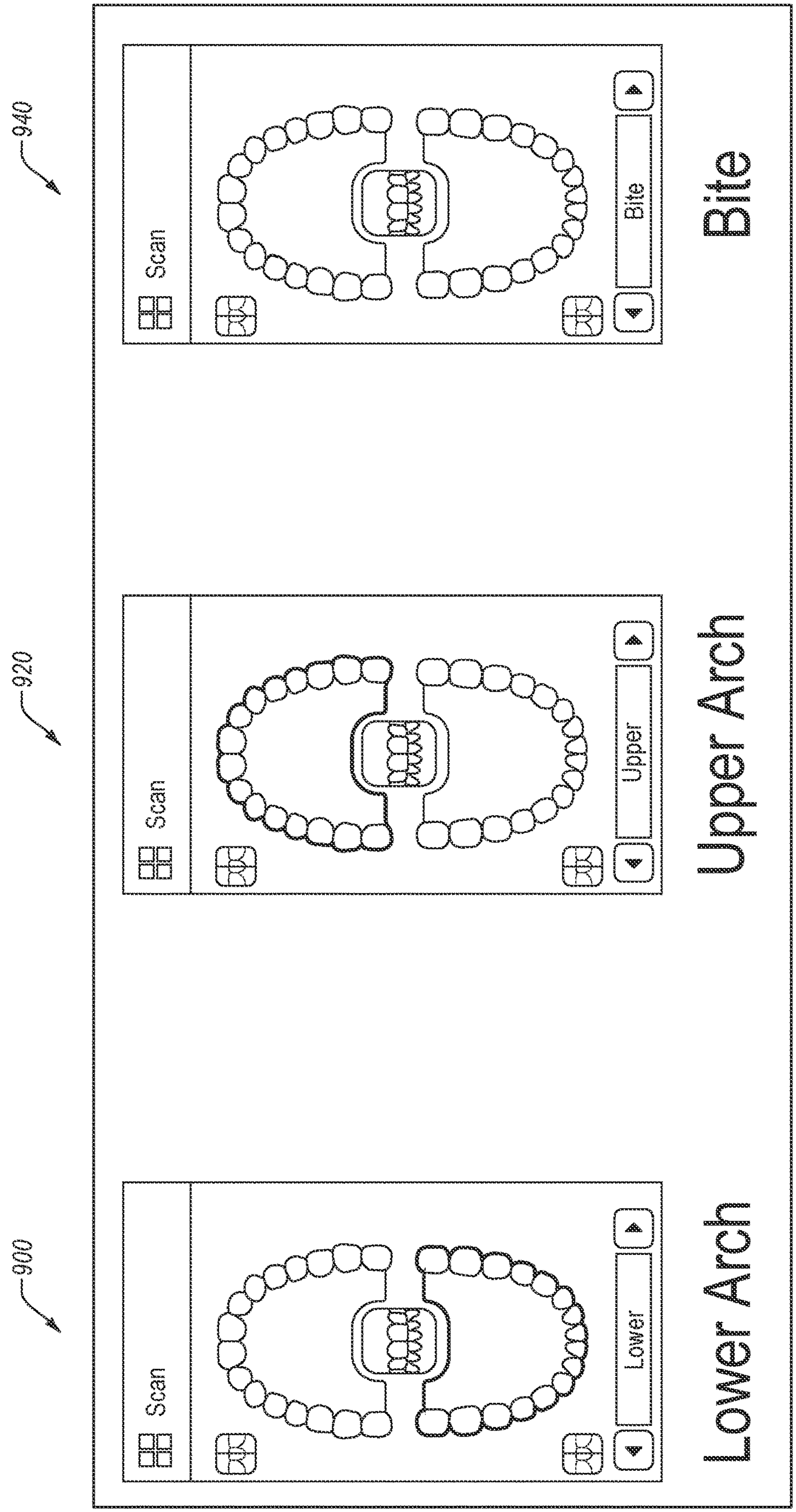
FIG. 9 illustrates a portion of a graphical user interface of an intraoral scan application showing different scanning roles or segments, in accordance with embodiments of the present disclosure.

FIG. 9 illustrates a portion of a graphical user interface (GUI) of an intraoral scan application showing different scanning roles or segments, in accordance with embodiments of the present disclosure. In one embodiment, a scan segment selector of a GUI for an intraoral scan application may include an upper dental arch segment graphic, a lower dental arch segment graphic, and a bite segment graphic. Depending on which segment is presently being scanned, a different one of the segment graphics may be highlighted. For example, visualization 900 shows selection of the lower dental arch segment, visualization 920 shows selection of the upper dental arch segment, and visualization 940 shows selection of the bite segment.

Figure 10A:
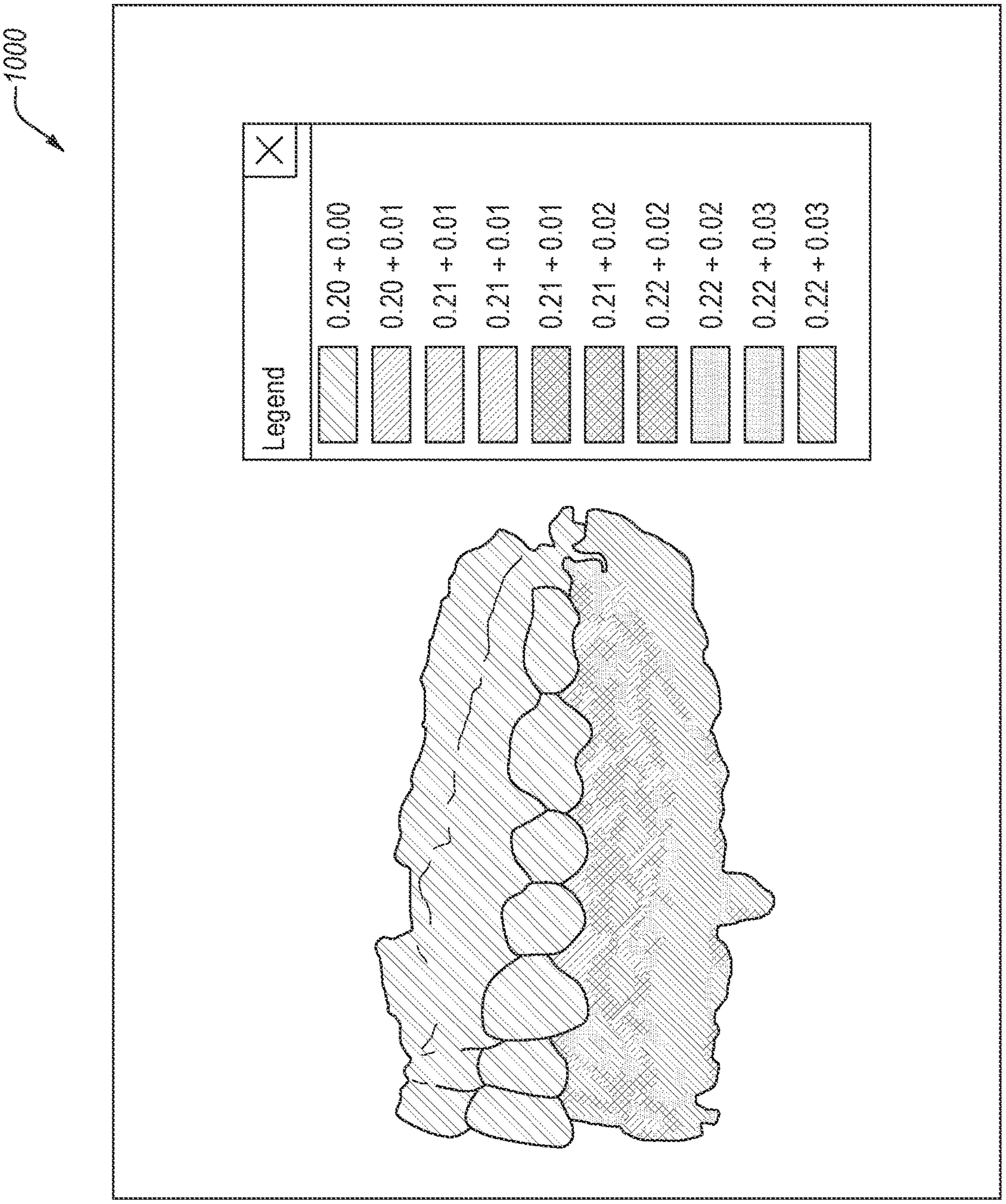
FIGS. 10A-B illustrate examples of relative movement of a lower dental arch for different scans of a patient bite, in accordance with embodiments of the present disclosure.
Figure 10B:
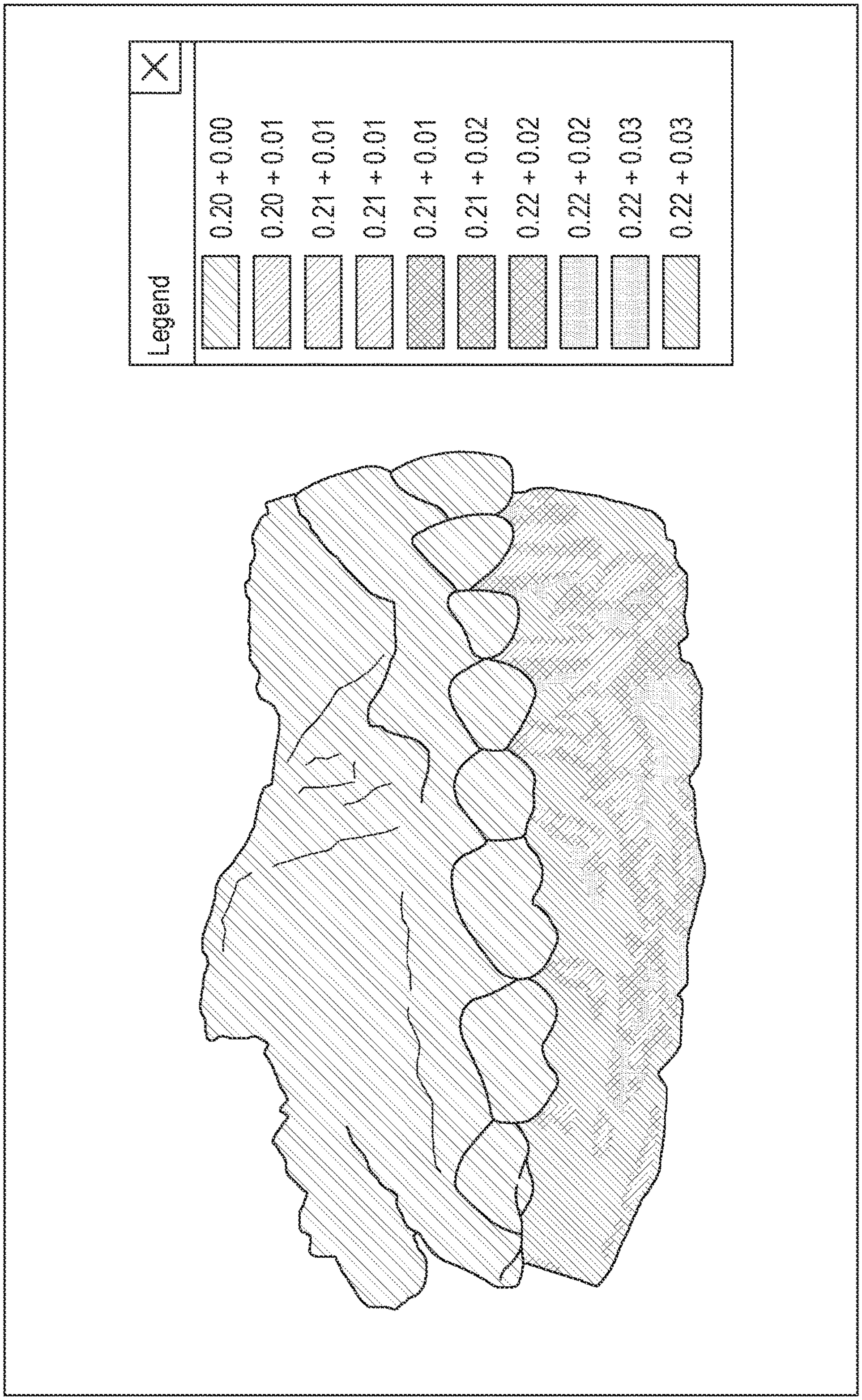

FIGS. 10A-B illustrate examples of relative movement of a lower dental arch for different scans of a patient bite, in accordance with embodiments of the present disclosure. Each of the figures is a heat map showing the magnitude of detected movement based on color and/or shading. FIG. 10A shows movement during a bite scan using a traditional bite scan protocol. FIG. 10B shows movement during bite scan using one of the bite scan protocols set forth herein, in accordance with embodiments of the present disclosure. As shown, the bite scan performed according to embodiments of the present disclosure had significantly less movement than the bite scan performed using the traditional bite scan protocol.

Figure 11:
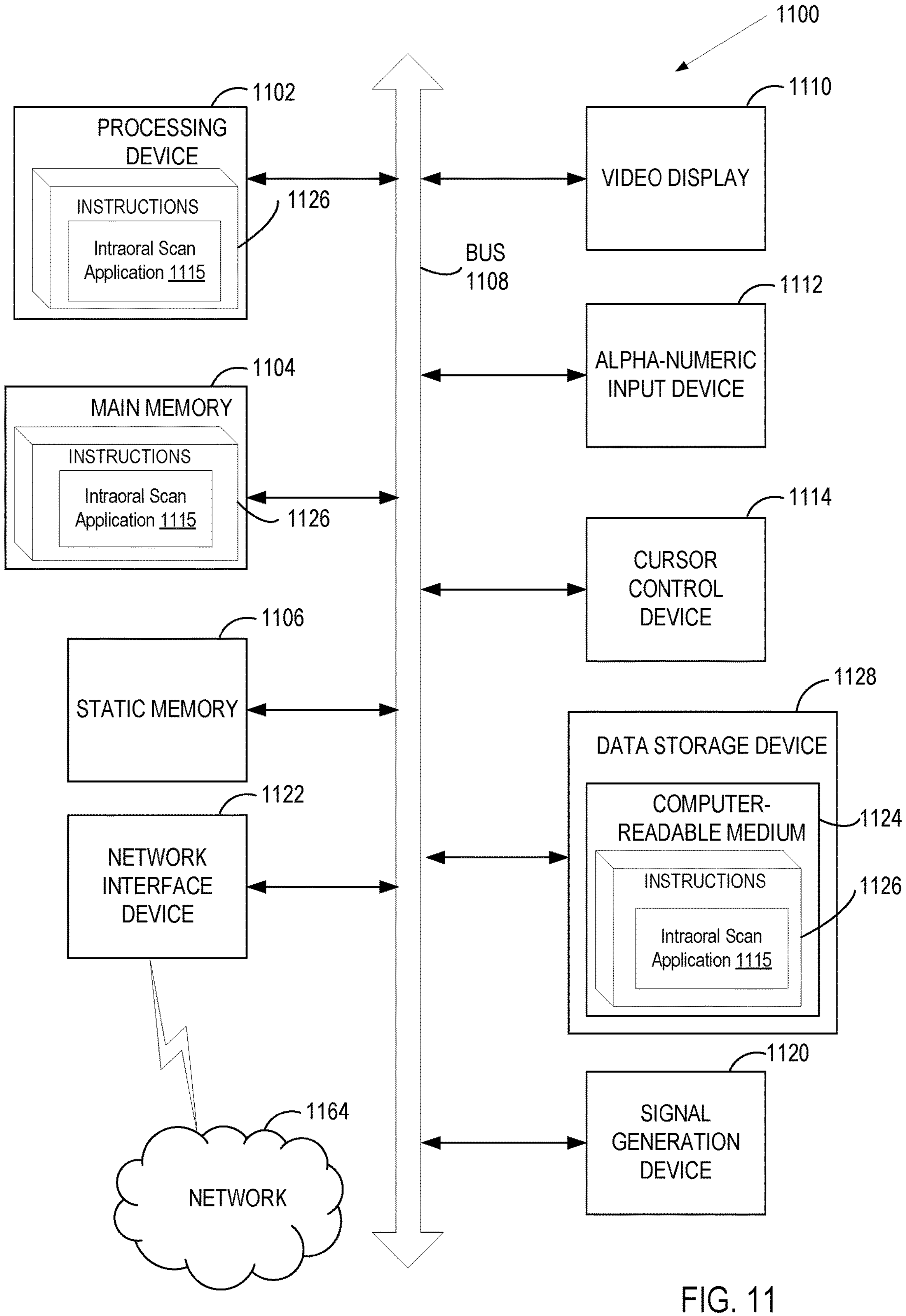
FIG. 11 illustrates a block diagram of an example computing device, in accordance with embodiments of the present disclosure.

FIG. 11 illustrates a diagrammatic representation of a machine in the example form of a computing device 1100 within which a set of instructions, for causing the machine to perform any one or more of the methodologies discussed herein, may be executed. In alternative embodiments, the machine may be connected (e.g., networked) to other machines in a Local Area Network (LAN), an intranet, an extranet, or the Internet. The computing device 1100 may correspond, for example, to computing device 105 and/or computing device 106 of FIG. 1A. The machine may operate in the capacity of a server or a client machine in a client-server network environment, or as a peer machine in a peer-to-peer (or distributed) network environment. The machine may be a personal computer (PC), a tablet computer, a set-top box (STB), a Personal Digital Assistant (PDA), a cellular telephone, a web appliance, a server, a network router, switch or bridge, or any machine capable of executing a set of instructions (sequential or otherwise) that specify actions to be taken by that machine. Further, while only a single machine is illustrated, the term "machine" shall also be taken to include any collection of machines (e.g., computers) that individually or jointly execute a set (or multiple sets) of instructions to perform any one or more of the methodologies discussed herein.

The example computing device 1100 includes a processing device 1102, a main memory 1104 (e.g., read-only memory (ROM), flash memory, dynamic random access memory (DRAM) such as synchronous DRAM (SDRAM), etc.), a static memory 1106 (e.g., flash memory, static random access memory (SRAM), etc.), and a secondary memory (e.g., a data storage device 1128), which communicate with each other via a bus 1108.

Processing device 1102 represents one or more general-purpose processors such as a microprocessor, central processing unit, or the like. More particularly, the processing device 1102 may be a complex instruction set computing (CISC) microprocessor, reduced instruction set computing (RISC) microprocessor, very long instruction word (VLIW) microprocessor, processor implementing other instruction sets, or processors implementing a combination of instruction sets. Processing device 1102 may also be one or more special-purpose processing devices such as an application specific integrated circuit (ASIC), a field programmable gate array (FPGA), a digital signal processor (DSP), network processor, or the like. Processing device 1102 is configured to execute the processing logic (instructions 1126) for performing operations and steps discussed herein.

The computing device 1100 may further include a network interface device 1122 for communicating with a network 1164. The computing device 1100 also may include a video display unit 1110 (e.g., a liquid crystal display (LCD) or a cathode ray tube (CRT)), an alphanumeric input device 1112 (e.g., a keyboard), a cursor control device 1114 (e.g., a mouse), and a signal generation device 1120 (e.g., a speaker).

The data storage device 1128 may include a machine-readable storage medium (or more specifically a non-transitory computer-readable storage medium) 1124 on which is stored one or more sets of instructions 1126 embodying any one or more of the methodologies or functions described herein, such as instructions for intraoral scan application 1115, which may correspond to intraoral scan application 115 of FIG. 1. A non-transitory storage medium refers to a storage medium other than a carrier wave. The instructions 1126 may also reside, completely or at least partially, within the main memory 1104 and/or within the processing device 1102 during execution thereof by the computer device 1100, the main memory 1104 and the processing device 1102 also constituting computer-readable storage media.

The computer-readable storage medium 1124 may also be used to store dental modeling logic 1150, which may include one or more machine learning modules, and which may perform the operations described herein above. The computer readable storage medium 1124 may also store a software library containing methods for the intraoral scan application 115. While the computer-readable storage medium 1124 is shown in an example embodiment to be a single medium, the term "computer-readable storage medium" should be taken to include a single medium or multiple media (e.g., a centralized or distributed database, and/or associated caches and servers) that store the one or more sets of instructions. The term "computer-readable storage medium" shall also be taken to include any medium other than a carrier wave that is capable of storing or encoding a set of instructions for execution by the machine and that cause the machine to perform any one or more of the methodologies of the present disclosure. The term "computer-readable storage medium" shall accordingly be taken to include, but not be limited to, solid-state memories, and optical and magnetic media.

It is to be understood that the above description is intended to be illustrative, and not restrictive. Many other embodiments will be apparent upon reading and understanding the above description. Although embodiments of the present disclosure have been described with reference to specific example embodiments, it will be recognized that the disclosure is not limited to the embodiments described, but can be practiced with modification and alteration within the spirit and scope of the appended claims. Accordingly, the specification and drawings are to be regarded in an illustrative sense rather than a restrictive sense. The scope of the disclosure should, therefore, be determined with reference to the appended claims, along with the full scope of equivalents to which such claims are entitled.

What is claimed is:

1. An intraoral scanning system, comprising:

an intraoral scanner to generate intraoral scan data of a bite of a patient;

a computing device, wherein the computing device is configured to:

receive the intraoral scan data of the bite of the patient during scanning of the bite of the patient, wherein a first datum and a second datum of the intraoral scan data each comprises an intraoral scan or a two-dimensional (2D) image, wherein the intraoral scan or the 2D image shows both a portion of a lower dental arch and a portion of an upper dental arch of the patient;

determine that the lower dental arch has moved relative to the upper dental arch during scanning of the bite based on a difference in a relative position of the lower dental arch to the upper dental arch between at least the first datum of the intraoral scan data and the second datum of the intraoral scan data exceeding a difference threshold; and perform a remedial action responsive to determining that the lower dental arch has moved relative to the upper dental arch during scanning of the bite of the patient.

2. The intraoral scanning system of claim 1, wherein the computing device is further to:

determine, for at least the first datum and the second datum of the intraoral scan data, the relative position of the lower dental arch to the upper dental arch.

3. The intraoral scanning system of claim 2, wherein the intraoral scan data comprises at least one of a plurality of intraoral scans or a plurality of 2D images, wherein the computing device is further to:

receive a first additional plurality of intraoral scans generated by the intraoral scanner during scanning of the upper dental arch of the patient;

generate a first three-dimensional (3D) model of the upper dental arch of the patient using the first additional plurality of intraoral scans;

receive a second additional plurality of intraoral scans generated by the intraoral scanner during scanning of the lower dental arch of the patient; and generate a second 3D model of the lower dental arch of the patient using the second additional plurality of intraoral scans.

4. The intraoral scanning system of claim 3, wherein the first datum comprises a first 2D image of the plurality of 2D images and the second datum comprises a second 2D image of the plurality of 2D images.

5. The intraoral scanning system of claim 4, wherein determining the relative position of the lower dental arch to the upper dental arch for the first 2D image comprises:

registering a first region of the first 2D image showing a portion of the upper dental arch to the first 3D model of the upper dental arch; and registering a second region of the first 2D image showing a portion of the lower dental arch to the second 3D model of the lower dental arch.

6. The intraoral scanning system of claim 3, wherein the first datum comprises a first intraoral scan of the plurality of intraoral scans and the second datum comprises a second intraoral scan of the plurality of intraoral scans.

7. The intraoral scanning system of claim 6, wherein determining the relative position of the lower dental arch to the upper dental arch for the first intraoral scan comprises:

registering a first region of the first intraoral scan showing a portion of the upper dental arch to the first 3D model of the upper dental arch; and registering a second region of the first intraoral scan showing a portion of the lower dental arch to the second 3D model of the lower dental arch.

8. The intraoral scanning system of claim 1, wherein the intraoral scan data comprises a plurality of intraoral scans, wherein the first datum comprises a first intraoral scan of the plurality of intraoral scans, wherein the second datum comprises a second intraoral scan of the plurality of intraoral scans, and wherein determining the difference in the relative position of the lower dental arch to the upper dental arch between at least the first datum of the intraoral scan data and the second datum of the intraoral scan data comprises:

identifying a first region of the first intraoral scan that shows a first portion of the upper dental arch;

identifying a second region of the first intraoral scan that shows a first portion of the lower dental arch;

determining a first relative position of the upper dental arch and the lower dental arch in the first intraoral scan based on the first region and the second region;

identifying a third region of the second intraoral scan that shows a second portion of the upper dental arch;

identifying a fourth region of the second intraoral scan that shows a second portion of the lower dental arch;

determining a second relative position of the upper dental arch and the lower dental arch in the second intraoral scan based on the third region and the fourth region; and comparing the second relative position of the upper dental arch and the lower dental arch to the first relative position of the upper dental arch and the lower dental arch.

9. The intraoral scanning system of claim 1, wherein performing the remedial action comprises notifying a user that the lower dental arch has moved relative to the upper dental arch during scanning of the bite of the patient.

10. The intraoral scanning system of claim 1, wherein the computing device is further to:

determine a difference in the relative position of the lower dental arch to the upper dental arch between a third datum of the intraoral scan data and at least one of the first datum or the second datum, wherein the third datum of the intraoral scan data comprises an intraoral scan or a 2D image that shows both a portion of the lower dental arch and a portion of the upper dental arch of the patient; and average the relative position of the lower dental arch to the upper dental arch from the third datum and the relative position of the lower dental arch to the upper dental arch from the at least one of the first datum or the second datum responsive to determining that the difference in the relative position of the lower dental arch to the upper dental arch between the third datum and the at least one of the first datum or the second datum is below the difference threshold.

11. The intraoral scanning system of claim 1, wherein performing the remedial action comprises recommending rescanning of the bite of the patient.

12. The intraoral scanning system of claim 1, wherein the computing device is further to:

determine a first subset of the intraoral scan data having a first relative position of the lower dental arch to the upper dental arch and a second subset of the intraoral scan data having a second relative position of the lower dental arch to the upper dental arch.

13. The intraoral scanning system of claim 12, wherein the computing device is further to:

prompt a user to select the first relative position of the lower dental arch to the upper dental arch or the second relative position of the lower dental arch to the upper dental arch; and receive a user selection of the first relative position of the lower dental arch to the upper dental arch.

14. The intraoral scanning system of claim 13, wherein the computing device is further to:

discard the second subset of the intraoral scan data.

15. The intraoral scanning system of claim 13, wherein the computing device is further to:

adjust the second subset of the intraoral scan data to have the first relative position of the lower dental arch to the upper dental arch.

16. The intraoral scanning system of claim 13, wherein the computing device is further to:

prompt the user to rescan a region of the bite of the patient associated with the second subset of the intraoral scan data.

17. The intraoral scanning system of claim 12, wherein the computing device is further to:

average the first relative position of the lower dental arch to the upper dental arch from the first subset of the intraoral scan data and the second relative position of the lower dental arch to the upper dental arch from the second subset of the intraoral scan data.

18. The intraoral scanning system of claim 12, wherein the computing device is further to:

generate a multi-bite solution comprising the first relative position of the lower dental arch to the upper dental arch and the second relative position of the lower dental arch to the upper dental arch.

19. The intraoral scanning system of claim 1, wherein performing the remedial action comprises prompting a user to rescan a portion of the bite of the patient.

20. A non-transitory computer readable medium comprising instructions that, when executed by a processing device, cause the processing device to perform operations comprising:

receiving intraoral scan data generated by an intraoral scanner during scanning of a bite of a patient, wherein a first datum and a second datum of the intraoral scan data each comprises an intraoral scan or a two-dimensional (2D) image, wherein the intraoral scan or the 2D image shows both a portion of a lower dental arch and a portion of an upper dental arch of the patient;

determining that the lower dental arch has moved relative to the upper dental arch during scanning of the bite based on a difference in a relative position of the lower dental arch to the upper dental arch between at least the first datum of the intraoral scan data and the second datum of the intraoral scan data exceeding a difference threshold; and performing a remedial action responsive to determining that the lower dental arch has moved relative to the upper dental arch during scanning of the bite of the patient.

21. The non-transitory computer readable medium of claim 20, the operations further comprising:

determining, for at least the first datum and the second datum of the intraoral scan data, the relative position of the lower dental arch to the upper dental arch.

22. The non-transitory computer readable medium of claim 21, wherein the intraoral scan data comprises at least one of a plurality of intraoral scans or a plurality of 2D images, the operations further comprising:

receiving a first additional plurality of intraoral scans generated by the intraoral scanner during scanning of the upper dental arch of the patient;

generating a first three-dimensional (3D) model of the upper dental arch of the patient using the first additional plurality of intraoral scans;

receiving a second additional plurality of intraoral scans generated by the intraoral scanner during scanning of the lower dental arch of the patient; and generating a second 3D model of the lower dental arch of the patient using the second additional plurality of intraoral scans.

23. The non-transitory computer readable medium of claim 20, wherein the intraoral scan data comprises a plurality of intraoral scans, wherein the first datum comprises a first intraoral scan of the plurality of intraoral scans, wherein the second datum comprises a second intraoral scan of the plurality of intraoral scans, and wherein determining the difference in the relative position of the lower dental arch to the upper dental arch between at least the first datum of the intraoral scan data and the second datum of the intraoral scan data comprises:

identifying a first region of the first intraoral scan that shows a first portion of the upper dental arch;

identifying a second region of the first intraoral scan that shows a first portion of the lower dental arch;

determining a first relative position of the upper dental arch and the lower dental arch in the first intraoral scan based on the first region and the second region;

identifying a third region of the second intraoral scan that shows a second portion of the upper dental arch;

identifying a fourth region of the second intraoral scan that shows a second portion of the lower dental arch;

determining a second relative position of the upper dental arch and the lower dental arch in the second intraoral scan based on the third region and the fourth region; and comparing the second relative position of the upper dental arch and the lower dental arch to the first relative position of the upper dental arch and the lower dental arch.

24. The non-transitory computer readable medium of claim 20, the operations further comprising:

determining a difference in the relative position of the lower dental arch to the upper dental arch between a third datum of the intraoral scan data and at least one of the first datum or the second datum, wherein the third datum of the intraoral scan data comprises an intraoral scan or a 2D image that shows both a portion of the lower dental arch and a portion of the upper dental arch of the patient; and averaging the relative position of the lower dental arch to the upper dental arch from the third datum and the relative position of the lower dental arch to the upper dental arch from the at least one of the first datum or the second datum responsive to determining that the difference in the relative position of the lower dental arch to the upper dental arch between the third datum and the at least one of the first datum or the second datum is below the difference threshold.

25. The non-transitory computer readable medium of claim 20, the operations further comprising:

determining a first subset of the intraoral scan data having a first relative position of the lower dental arch to the upper dental arch and a second subset of the intraoral scan data having a second relative position of the lower dental arch to the upper dental arch;

prompting a user to select the first relative position of the lower dental arch to the upper dental arch or the second relative position of the lower dental arch to the upper dental arch; and receiving a user selection of the first relative position of the lower dental arch to the upper dental arch.

26. The non-transitory computer readable medium of claim 20, wherein the difference in the relative position of the lower dental arch to the upper dental arch corresponds to a movement or shift in a position of the lower dental arch relative to the upper dental arch.

* * * * *